United States Patent
Omote

(10) Patent No.: US 7,035,373 B2
(45) Date of Patent: Apr. 25, 2006

(54) X-RAY DIFFRACTION APPARATUS

(75) Inventor: Kazuhiko Omote, Akiruno (JP)

(73) Assignee: Rigaku Corporation, Tokyo (JP)

( * ) Notice: Subject to any disclaimer, the term of this patent is extended or adjusted under 35 U.S.C. 154(b) by 1 day.

(21) Appl. No.: 10/802,139

(22) Filed: Mar. 17, 2004

(65) Prior Publication Data

US 2004/0190681 A1    Sep. 30, 2004

(30) Foreign Application Priority Data

Mar. 26, 2003   (JP) ............................. 2003-084055

(51) Int. Cl.
   *G01N 23/20*    (2006.01)
(52) U.S. Cl. ............................. 378/79; 378/81; 378/71
(58) Field of Classification Search ............ 378/79–81, 378/71, 85

See application file for complete search history.

(56) References Cited

U.S. PATENT DOCUMENTS

| | | | |
|---|---|---|---|
| 6,014,423 A * | 1/2000 | Gutman et al. ................ | 378/85 |
| 6,069,934 A * | 5/2000 | Verman et al. ................ | 378/73 |
| 6,282,263 B1 | 8/2001 | Arndt et al. | |
| 2003/0068010 A1* | 4/2003 | Lentfer ......................... | 378/81 |

FOREIGN PATENT DOCUMENTS

JP    11-304731 A    11/1999

OTHER PUBLICATIONS

X. X. Jiang et al: "Study of Strain and Composition of the Self-Organized GE Dots by Grazing Incident X-Ray Diffraction", Nuclear Instruments & Methods in Physics Research Section—A: Accelerators, Spectrometers, Detectors and Associated Equipment, North-Holland Publishing Company, Amsterdam, NL, vol. 467-468, Jul. 21, 2001, pp. 362-365, XP004297870, ISSN: 0168-9002. * Chapter "2. Experimental" on pp. 363-364.—* reference 12*.

(Continued)

*Primary Examiner*—Craig E. Church
*Assistant Examiner*—Krystyna Suchecki
(74) *Attorney, Agent, or Firm*—Frishauf, Holtz, Goodman & Chick, P.C.

(57) ABSTRACT

An -ray emitted from an incident optical system is incident on a sample supported by a sample support mechanism, and a diffracted X-ray is detected by a receiving optical system. The incident optical system includes an X-ray source and a multilayer-film mirror. An attitude controlling unit of the sample support mechanism switches a condition of the sample support mechanism from a state maintaining the sample to have a first attitude in which a normal line of the surface of the sample is parallel with a first axis of rotation to another state maintaining the sample to have a second attitude in which the normal line of the surface of the sample is perpendicular to the first axis of rotation. When the receiving optical system is rotated around the first axis of rotation while maintaining the sample in the first attitude, in-plane diffraction measurement is possible. On the other hand, when the receiving optical system is rotated in the same way while maintaining the sample in the second attitude, out-of-plane diffraction measurement is possible.

7 Claims, 23 Drawing Sheets

OTHER PUBLICATIONS

X. Jiang et al: "Status of the 4WIC Beamline and the Diffuse Scattering Experimental Station at the Beijing Synchrotron Radiation Facility", Nuclear Instruments & Methods in Physics Research Section—B: Beam Interactions With Materials and Atoms, North-Holland Publishing Company, Amsterdam, NL, vol. 129, No. 4, Sep. 1, 1997, pp. 543-547, XP004089038, ISSN: 0168-583X. *Chapter "3. X-Ray Diffuse Scattering Station"—*Figure 2*.

M. S. Goorsky et al: "Grazing Incidence In-Plane Deffraction Measurement of In-Plane Mosaic With Microfocus X-Ray Tubes", Crystal Resear H and Technology, 2002, Wiley-VCH Verlag Berlin GmbH, Germany, "Online!", vol. 37, No. 7, pp. 645-653, XP002289273, ISSN: 0232-1300, Retrieved from the Internet: <URL:http://www.crystalresearch.com/crt/ab37/645_a.pdf>, retrieved on Jul. 21, 2004?, *Chapter "Experimental Requirements"*.

"Bede D1 With Microscope", UCLA Materials Science & Engineering, Online! Nov. 12, 2002, XP002289274, Retrieved from the Internet: <URL:http://www.seas.ucla.edu/igoorsky/xray/Dlmicro. .html>, retrieved on Jul. 21, 2004!, *the whole document*.

Licai Jiang et al: "Application of Multilayer Optics to X-Ray Diffraction Systems", The Rigaku Journal, Online!, vol. 18, No. 2, 2001, pp. 13-22, XP002289275, Retrieved from the Internet: ,URL:http://www.rigakumsc.com/journal/Vol18.2.2001/Jiang.pdf>, retrieved on Jul. 21, 2004!, *p. 19, last paragraph—p. 20, paragraph 1, Figure 13.*

K. Omote: "Direct Observation of In-Plane Texture in Cobalt Recording Media by Means of a Laboratory-Scale X-Ray Diffractometer", X-Ray Spectrometry, Nov.-Dec. 1999, Wiley, U.K., vol. 28, No. 6, pp. 440-445, XP009034007, ISSN: 0049-8246—*p. 442*.

B. Verman: "Microfocusing Source and Multilayer Optics Based X-Ray Diffraction Systems", The Rigaku Journal, Online!, vol. 19, No. 1, 2002, pp. 4-13, XP002289276, Retrieved from the Internet: <URL:http://www.riguksc.com/journal/Vol19.1.2002/verman.pdf>, retrieved on Jul. 21, 2004, *p. 4*, *p. 8, right-hand column, line 5—line 19; table 4*.

A. K. Malhotra et al: "In Situ/Ex Situ X-Ray Analysis System for Thin Sputtered Films", Surf Coat Technol.; Surface & Coatings Technology, Nov. 10, 1998, Elsevier Science S.A., Lausanne, Switzerland, vol. 110, No. 1-2, Nov. 10, 1998, pp. 105-110, XP002288818—*p. 106*.

"Ultima III", Rigaku, Online!, Feb. 4, 2004, XP002289277, Retrieved from the Internet: <URLLhttp://www.rigakumsc.com/xrd/ultima.html>, retrieved on Jul. 21, 2002, *the whole document*.

Y. Hirai et al: "The Design and Performance of Beamline BL16XU at Spring-8", Nuclear Instruments & Methods in Physics Research, Section—A: Accelerators, Spectrometers, Detectors and Associated Equipment, North-Holland Publishing Company, Amsterdam, NL, vol. 251, No. 2-3, Apr. 2, 2004, pp. 538-548, XP004498331, ISSN: 0168-9002, *Chapter "2.5..2. X-ray diffractometer system", on pp. 545, 546*—reference 22*.

R. Baudoing-Savois, et al., "A new UHV diffractometer for surface structure and real time molecular beam deposition studies with synchrotron radiations at ESRF," Nuclear Instruments and Methods in Physics Research B 149 (1999), pp. 213-227.

H. Oyangi, et al., "A new apparatus for surface x-ray absorption and diffraction studies using synchrotron radiation," Review of Scientific Instrument 66, Dec., 1995, Woodbury, New York, U.S.A., pp. 5477-5485.

* cited by examiner

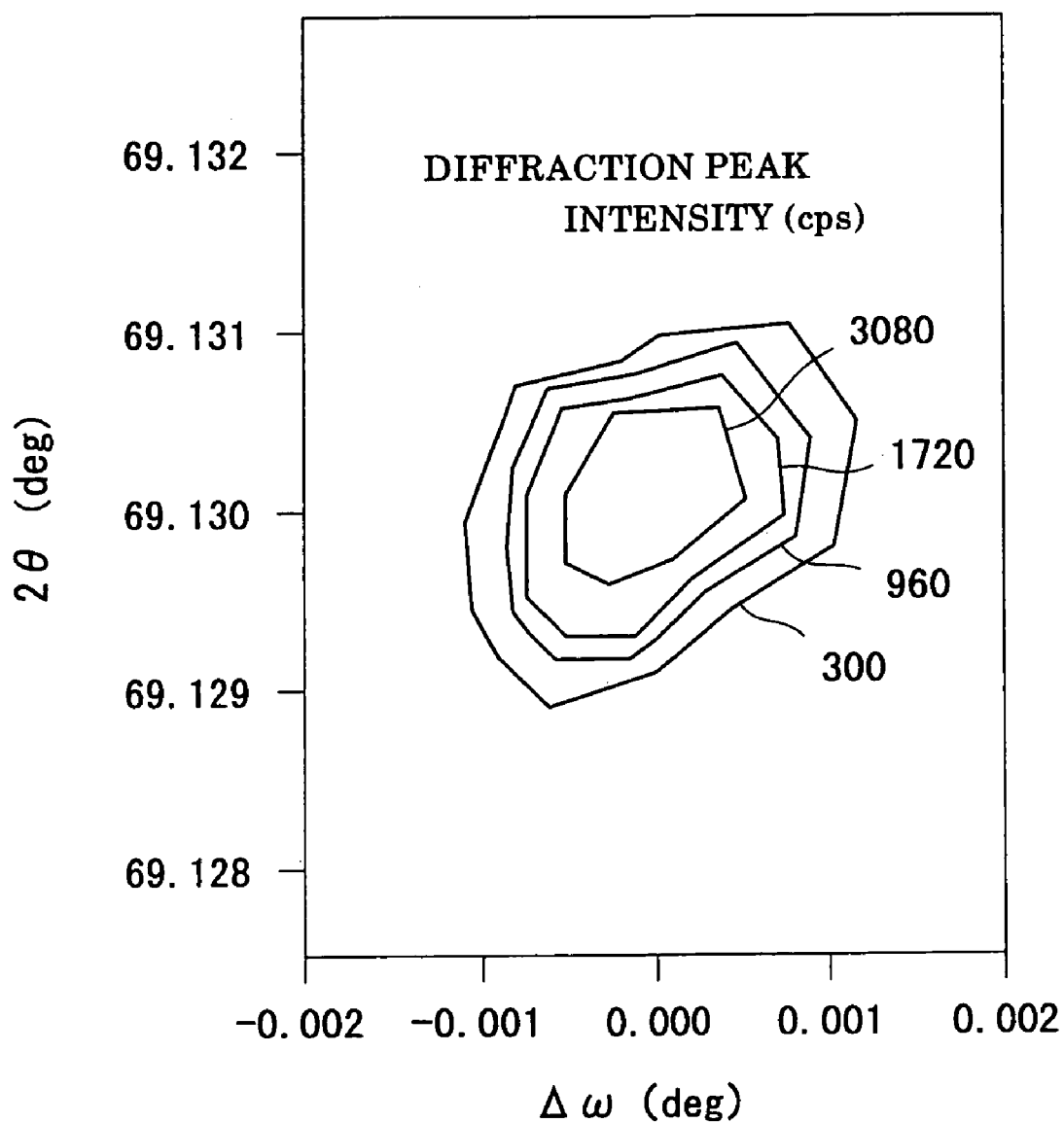

ively small incident angle of about 0.1° to 0.5°, for
X-RAY DIFFRACTION APPARATUS

BACKGROUND OF THE INVENTION

1. Field of the Invention

The present invention relates to an X-ray diffraction apparatus making it possible to execute in-plane diffraction measurement.

2. Description of the Related Art

The in-plane diffraction measurement, as shown in FIG. 1A, designates a measuring technique in that an X-ray 12 is incident on a sample surface 10 at a grazing incident angle α (a very small incident angle of about 0.1° to 0.5°, for example) and a diffracted X-ray 14 is detected at an outgoing angle β grazing from the sample surface 10. A circle 16 indicated by an imaginary line denotes a plane including the sample surface 10. The in-plane diffraction is a phenomenon in which an X-ray is diffracted on a crystal lattice surface substantially perpendicular to the sample surface. Since the diffracted X-ray is detected within a plane substantially flush with the plane 16 including the sample surface 10, this technique is called as in-plane. When the in-plane diffraction measurement is employed, crystal information only in the vicinity of the sample surface is obtained, so that the in-plane diffraction measurement is especially used in analyses of a thin film sample.

On the other hand, in the general case in which an X-ray diffraction is generally measured using an X-ray diffractometer, as shown in FIG. 1B, the diffracted X-ray 14 is detected within a plane 20 including both the normal line 18 of the sample surface 10 and the incident X-ray 12. Such a general measuring technique will be called as, in this specification, out-of-plane diffraction measurement against the in-plane diffraction measurement. Thinking about measurement of a thin film sample with the out-of-plane diffraction measurement, it also requires that an X-ray 12 is incident on the sample surface 10 at a grazing incident angle α for reducing the effect of a substrate under the thin film. Accordingly, the out-of-plane diffraction measurement of the thin film sample would become a so-called asymmetrical X-ray diffraction measurement in that a diffraction pattern is measured with the fixed incident angle α relative to the sample surface 10. In this case, an optical system to be used is not for a focusing method but for a parallel beam method.

The in-plane diffraction measurement requires a dedicated apparatus different from a general X-ray diffraction apparatus. There is a desire, however, that both the in-plane and the out-of-plane diffraction measurement can be made with the use of a common X-ray diffraction apparatus. An X-ray diffraction apparatus satisfying the desire is known as disclosed in Japanese Patent Publication No. 11-304731 A (1999). The procedure of the in-plane diffraction measurement of a thin film sample using this prior-art apparatus is as follows: the sample surface is get upright; an X-ray detector is arranged to turn around a horizontal axis of rotation (i.e., turn in a vertical plane); an X-ray which travels horizontally is incident on the sample surface at a grazing angle; and the X-ray detector is rotated in a vertical plane so as to detect an in-plane diffracted X-ray from the sample surface.

On the other hand, the procedure of X-ray diffraction measurement with a θ–2θ scan (i.e., the out-of-plane diffraction measurement) using the same apparatus is as follows: the sample surface is get upright in the same way as in the in-plane diffraction measurement; the X-ray detector is arranged to turn around a vertical axis of rotation (i.e., turn in the horizontal plane) different from the in-plane diffraction measurement; the sample is rotated around the vertical axis of rotation by an angle θ relative to an incident X-ray which travels horizontally; and the X-ray detector is rotated around the same axis of rotation as the θ rotation by an angle 2θ so as to detect a diffracted X-ray from the sample surface. If a thin film sample is to be measured with the out-of-plane diffraction measurement using this X-ray diffraction apparatus, another procedure is also effective in that a diffracted X-ray is measured using the parallel beam in which an X-ray is incident on the sample surface at a grazing angle and only the X-ray detector is rotated around the vertical axis of rotation.

If the above-mentioned known X-ray diffraction apparatus is used, both the out-of-plane diffraction measurement and the in-plane diffraction measurement can be made for a thin film sample, in principle. In the out-of-plane diffraction measurement, the X-ray detector is rotated within a horizontal plane, and such rotation of the X-ray detector is achieved with the conventional goniometer, enabling the angular control to be performed with a high degree of accuracy. Accordingly, the resolution of the detected diffraction angle is superior. On the other hand, in the in-plane diffraction measurement, the same X-ray detector must be rotated within a vertical plane, so that it is difficult to have the high-accuracy angular control because of the rotation against the gravitation. Even if the high accuracy rotation is achieved within the vertical plane, the rotational control mechanism would become expensive for the rotation of the X-ray detector with a high degree of accuracy within both the horizontal plane and the vertical plane.

SUMMARY OF THE INVENTION

It is an object of the present invention to provide an X-ray diffraction apparatus making it possible to perform both the out-of-plane diffraction measurement and the in-plane diffraction measurement with a high degree of resolution in both measurement.

An X-ray diffraction apparatus according to the present invention is characterized by the following. For easier understanding, reference numerals corresponding to elements according to the embodiment shown in FIGS. 2 to 5 are shown in parentheses; however, the present invention is not limited to this embodiment.

An X-ray diffraction apparatus according to the present invention comprises an incident optical system (22), a sample support mechanism (24), a receiving optical system (26), and receiving-optical-system rotating means (30). An X-ray emitted from the incident optical system (22) is incident on a sample (60) supported by the sample support mechanism (24), and an X-ray diffracted by the sample (60) is detected by the receiving optical system (26). The receiving-optical-system rotating means (30) has a function to allow the receiving optical system (26) to turn around a first axis of rotation (32) for changing an angle (2θ) defined by the direction of the X-ray incident on the sample (60) and the optical axis of the receiving optical system (26). The incident optical system (22) includes an X-ray source (66) and a multilayer-film mirror (76) which has a function to collimate an X-ray emitted from the X-ray source (66) within a plane perpendicular to the first axis of rotation (32). The sample support mechanism (24) includes attitude controlling means (36, 40) which has a function to switch the condition of the sample support mechanism (24) from a state maintaining the sample (60) to have a first attitude so that a normal line (61) of the surface of the sample (60) is substantially parallel with the first axis of rotation (32) to another state maintaining the sample (60) to have a second attitude so that the normal line (61) of the surface of the sample (60) is substantially perpendicular to the first axis of rotation (32). The sample support mechanism (24) also includes first incident-angle controlling means (36, 40) which has a function to rotate the sample (60) around a second axis of rotation (37) that is substantially perpendicular to the first axis of rotation (32) for changing an incident angle ($\alpha$) when an X-ray emitted from the incident optical system (22) is incident on the surface of the sample (60) that is in the first attitude. The sample support mechanism (24) further includes second incident-angle controlling means (34) which has a function to rotate the sample (60) around the first axis of rotation (32) for changing the incident angle ($\alpha$) when an X-ray emitted from the incident optical system (22) is incident on the surface of the sample (60) that is in the second attitude.

When the receiving optical system is rotated around the first axis of rotation while maintaining the sample in the first attitude, the in-plane diffraction measurement is possible. On the other hand, when the receiving optical system is rotated around the same first axis of rotation while maintaining the sample in the second attitude, the out-of-plane diffraction measurement is possible. Therefore, according to the present invention, both the in-plane and out-of-plane diffraction measurement can be performed with a high degree of resolution as long as the degree of resolution could be improved within the common diffraction plane only.

The attitude controlling means (36, 40) and the first incident-angle controlling means (36, 40) may be realized with a common mechanism (36, 40).

The multilayer-film mirror (76) may be of a type having a first reflection surface (96) with a parabolic curve for collimating an X-ray within a first plane (X-Y plane) perpendicular to the first axis of rotation (32) and a second reflection surface (97) with a parabolic curve for collimating an X-ray within a second plane (Y-Z plane) perpendicular to the first plane (X-Y plane). Using the multilayer-film mirror of the type, the incident X-ray is collimated not only within the diffraction plane but also within a plane perpendicular to the diffraction plane, so that the divergence of the incident angle ($\alpha$) can be reduced, suitable for measuring variation in information in the sample depth direction, for example.

The multilayer-film mirror (76) may be of another type having a first reflection surface (96) with a parabolic curve for collimating an X-ray within a first plane (X-Y plane) perpendicular to the first axis of rotation (32) and a second reflection surface (97a) with an elliptical-arc curve for focusing an X-ray on the sample within a second plane (Y-Z plane) perpendicular to the first plane (X-Y plane). Using the multilayer-film mirror of the type, since an X-ray is focused within a plane perpendicular to the diffraction plane, the X-ray irradiation intensity is increased on a sample, suitable for measurement requiring a higher intensity.

The receiving optical system (26) may also be rotated around the second axis of rotation (37), so that the in-plane diffraction can be measured with a scan of the outgoing angle $\beta$.

The sample support mechanism (24) may include a six-axis movement mechanism: a mechanism for moving the sample in a direction (W-direction) perpendicular to the surface of the sample; a mechanism for translating the sample in a two-dimensional direction (U- and V-directions) within a plane parallel with the surface of the sample; a mechanism for rotating the sample (Ru and Rv rotations) around two axes of rotation which are orthogonal to each other and pass on the surface of the sample; and a mechanism for an in-plane rotation of the sample ($\phi$ rotation).

BRIEF DESCRIPTION OF THE DRAWINGS

FIG. 17 is a graph of measured results in the measurement example 1;

DESCRIPTION OF THE PREFERRED EMBODIMENTS

Figure 2:
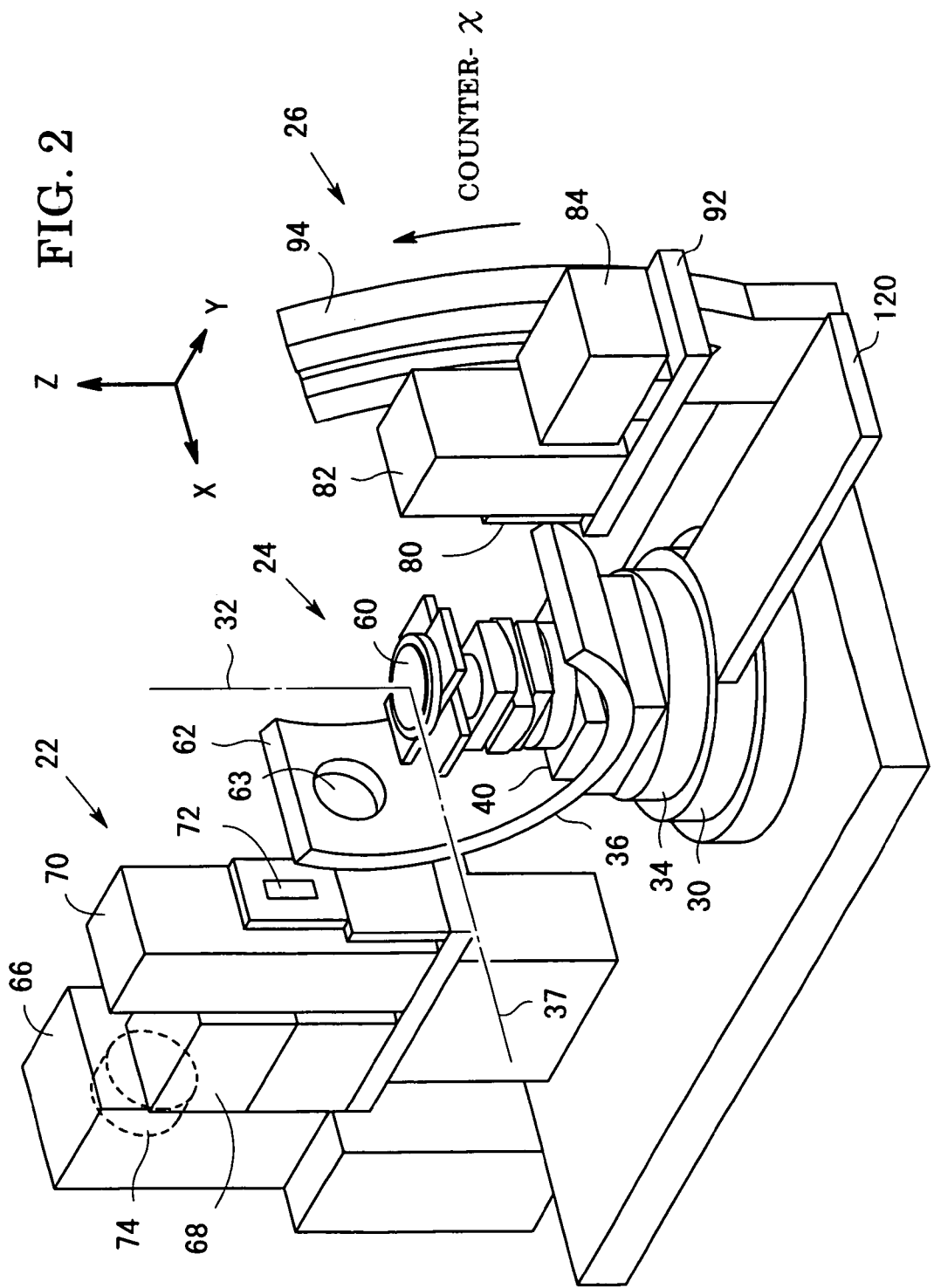
FIG. 2 is a perspective view of an X-ray diffraction apparatus according to an embodiment of the present invention.

An embodiment according to the present invention will be described below with reference to the drawings. FIG. 2 is a perspective view of an X-ray diffraction apparatus according to the embodiment. The X-ray diffraction apparatus includes an incident optical system 22, a sample support mechanism 24, a receiving optical system 26, and an receiving-optical-system turntable 30.

Figure 3:
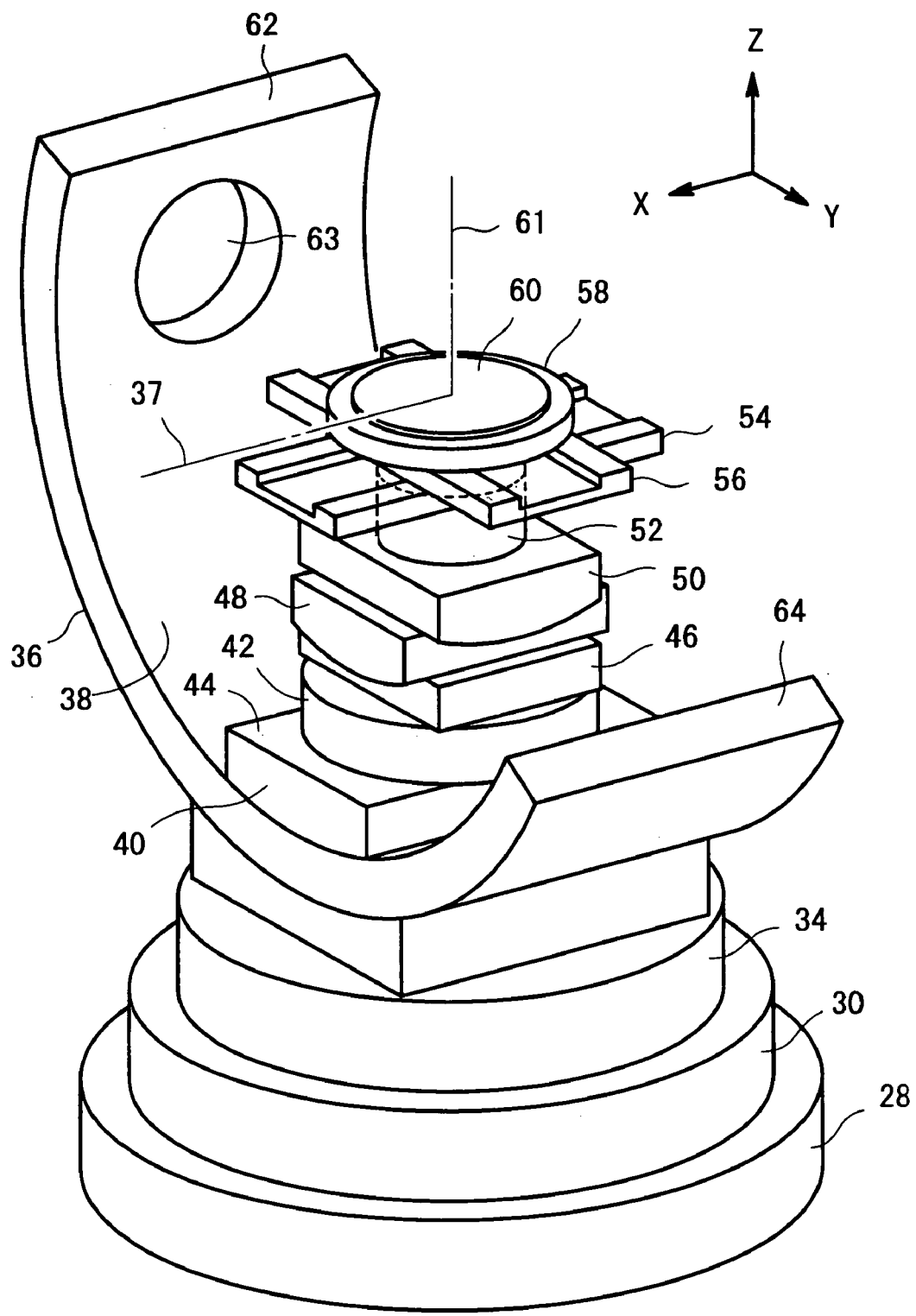
FIG. 3 is a perspective view of a sample support mechanism and a receiving-optical-system turntable.
Figure 4:
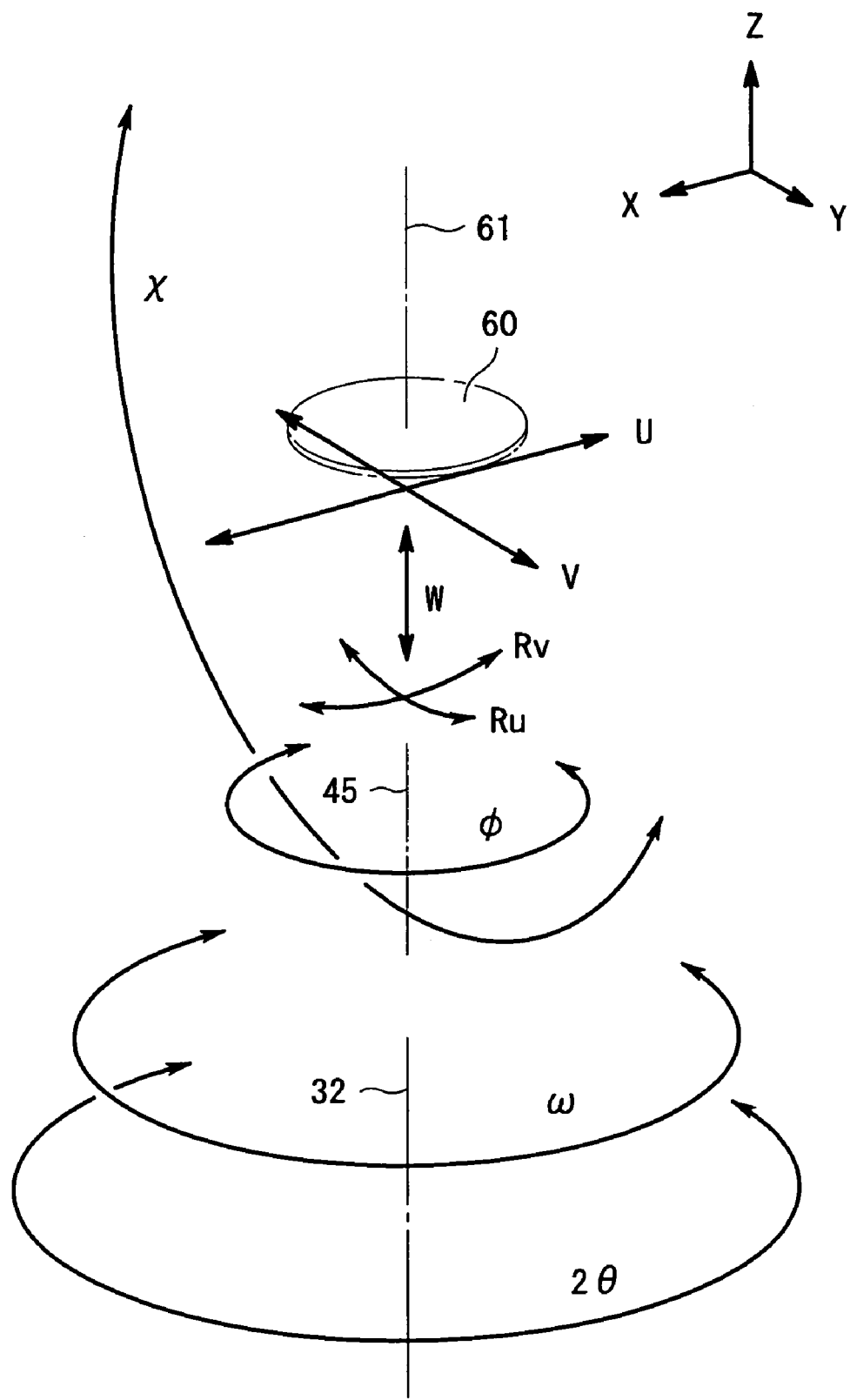
FIG. 4 is a perspective view showing movements of the sample support mechanism and the receiving-optical-system turntable.

First, the sample support mechanism 24 and the receiving-optical-system turntable 30 will be described. FIG. 3 is a perspective view of the sample support mechanism 24 and the receiving-optical-system turntable 30 and FIG. 4 is a perspective view showing their movements only. Referring to FIGS. 3 and 4, an X-axis and a Y-axis are defined in a horizontal plane, and a Z-axis is defined to be perpendicular to the horizontal plane, resulting in a three-dimensional rectangular coordinate system. A stationary base 28 is provided with the receiving-optical-system turntable 30 which can turn around an axis of rotation 32 (see FIG. 4) with respect to the base 28. This rotation will be referred to as a 2θ rotation. The axis of rotation 32 extends in the vertical direction, parallel with the Z-axis. The receiving optical system 26 is fixed to the receiving-optical-system turntable 30, as will be described later, so that the entire receiving optical system 26 can turn in a horizontal plane. A mechanism for the 2θ rotation can be a high-resolution rotation control mechanism with an angle repeatability of $1/10,000°$, for example,.

Among the components shown in FIG. 3, the receiving-optical-system turntable 30 does not belong to the sample support mechanism 24 because the turntable 30 does not relate to supporting of a sample. The components other than the receiving-optical-system turntable 30 belong to the sample support mechanism 24.

The base 28 is also provided with a curved-guide turntable 34 that is rotatable around the axis of rotation 32 with respect to the base 28. This rotation is referred to as an ω rotation (see FIG. 4). Rotating the curved-guide turntable 34, a curved guide 36 fixed thereon can be rotated in a horizontal plane. The receiving-optical-system turntable 30 and the curved-guide turntable 34 can be rotated independently from each other. A mechanism for the ω rotation can also be a high-resolution rotation control mechanism.

The curved guide 36 is fixed on the curved-guide turntable 34. One end 62 of the curved guide 36 is located at a position higher than a sample 60, and a through-hole 63 for an X-ray is formed in the vicinity of the one end 62. The through-hole 63 allows an incident X-ray to pass through the curved guide 36 during the in-plane diffraction measurement. The other end 64 of the curved guide 36 is located at a position lower than the sample 60.

The curved guide 36 has a circular-arc internal surface 38 on which an attitude-change table 40 is arranged for rotation around a horizontal axis of rotation 37 within an angular range of about 90° along the internal surface 38 of the curved guide 36. This rotation will be referred to as a χ (chi in Greek alphabet) rotation (see FIG. 4). When the attitude-change table 40 comes to the position shown in FIG. 3, the sample 60 is substantially horizontal in attitude, and at-this time, the in-plane diffraction can be measured. When the attitude-change table 40 moves along the internal surface 38 of the curved guide 36 to the vicinity of the one end 62 of the curved guide 36, the sample 60 becomes vertical in attitude, and at this time, the out-of-plane diffraction can be measured.

The attitude-change table 40 has an upper surface on which a sample turntable 42 is arranged for rotation around an axis of rotation 45 (see FIG. 4) perpendicular to the upper surface 44 of the attitude-change table 40. This rotation will be referred to as a φ rotation (see FIG. 4). The φ rotation enables the sample 60 to turn with an in-plane rotation.

The sample turntable 42 has an upper surface to which an adjustment-table support table 46 is fixed. The adjustment-table support table 46 has an upper surface which is a curved surface of a concave arc shape on which a first adjustment table 48 is arranged for movement along the curved surface. The first adjustment table 48 has a bottom surface which is a curved surface of a downwardly convex arc shape so as to fit the concave curved surface of the upper surface of the adjustment-table support table 46. The first adjustment table 48 can move along the curved surface of the adjustment-table support table 46 so as to turn around an axis of rotation, which is coaxial with the axis of rotation 37 of the attitude-change table 40, within a range of a very small angle relative to the adjustment-table support table 46. This rotation will be referred to as an Ru rotation (see FIG. 4). The first adjustment table 48 has an upper surface which is also a curved surface of a concave arc shape, on which a second adjustment table 50 is arranged for movement along the curved surface. The second adjustment table 50 has a bottom surface which is also a curved surface of a downwardly convex arc shape so as to fit the concave curved surface of the upper surface of the first adjustment table 48. The second adjustment table 50 can move along the curved surface of the first adjustment table 48 so as to turn around a horizontal axis of rotation within a range of a very small angle relative to the first adjustment table 48. This rotation will be referred to as an Rv rotation (see FIG. 4). Both the axis of rotation of the first adjustment table 48 and the axis of rotation of the second adjustment table 50 pass on the surface of the sample 60, and they are orthogonal to each other. The first adjustment table 48 and the second adjustment table 50 are for fine adjustment of the attitude of the sample 60 with respect to the sample turntable 42, and their rotations within a range of a very small angle allow a normal line 61 of the surface of the sample 60 to be coincide with the axis of rotation 45 (see FIG. 4) of the sample turntable 42.

The second adjustment table 50 is provided with an elevating pedestal 52 that is movable in a direction perpendicular to the upper surface of the second adjustment table 50, i.e., it is movable in a W-direction in FIG. 4. Assuming that the upper surface of the second adjustment table 50 is horizontal as shown in FIG. 3, the elevating pedestal 52 can move up and down in a Z-direction. The movement in the W-direction is for a movement of the sample surface to an X-ray irradiation position, depending on the thickness of the sample 60. The elevating pedestal 52 has an upper surface on which a first translation guide 54 is fixed. The first translation guide 54 has an upper surface on which a second translation guide 56 is arranged for sliding movement. The second translation guide 56 is movable in the first translational direction along a guide groove formed on the upper surface of the first translation guide 54, i.e., it is movable in a U-direction in FIG. 4. In the state shown in FIG. 3, the moving direction of the second translation guide 56 coincides with the X-direction. The second translation guide 56 has an upper surface on which a sample table 58 is arranged for sliding movement. The sample table 58 is movable in the second translational direction along a guide groove formed on the upper surface of the second translation guide 56, i.e., it is movable in a V-direction of FIG. 4. In the state shown in FIG. 3, the moving direction of the sample table 58 coincides with the Y-direction. The first and second translational directions are orthogonal to each other. The sample table 58 has an upper surface on which the sample 60 can be mounted. The translational movements of the second translation guide 56 and the sample table 58 allow the sample 60 to be moved in the two-dimensional directions within a surface parallel to the sample surface, resulting in a change of an X-ray irradiation position on the sample surface.

Figure 5:
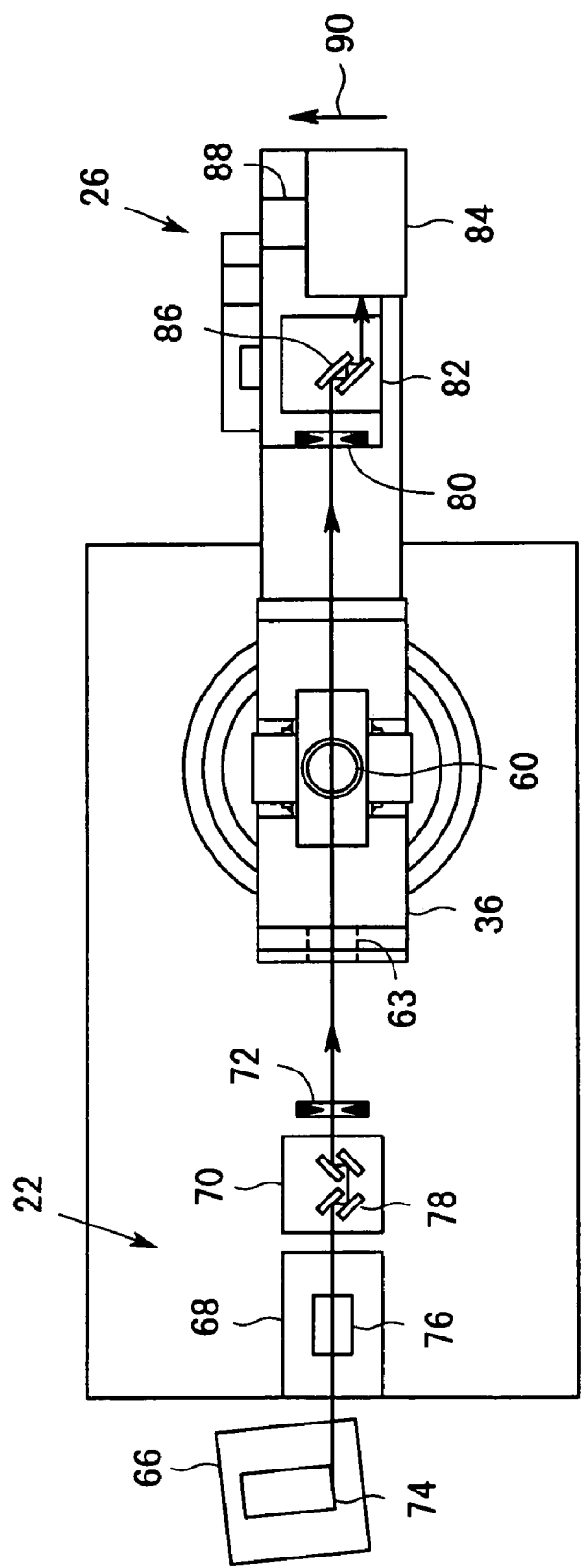
FIG. 5 is a plan view of the X-ray diffraction apparatus shown in FIG. 2.

Next, the incident optical system 22 will be described with reference to FIGS. 2 and 5; FIG. 5 is a plan view of the X-ray diffraction apparatus shown in FIG. 2, partly showing the inside of the apparatus. The incident optical system 22 includes an X-ray tube 66, a multilayer-film mirror device 68, an incident-monochromator device 70, and an incident-slit device 72. The X-ray tube 66 includes a rotating target 74, which revolves around a horizontal axis of rotation for generating an X-ray with a point focus. The multilayer-film-mirror device 68 accommodates a multilayer-film mirror 76 therein (see FIG. 5).

Figure 6:
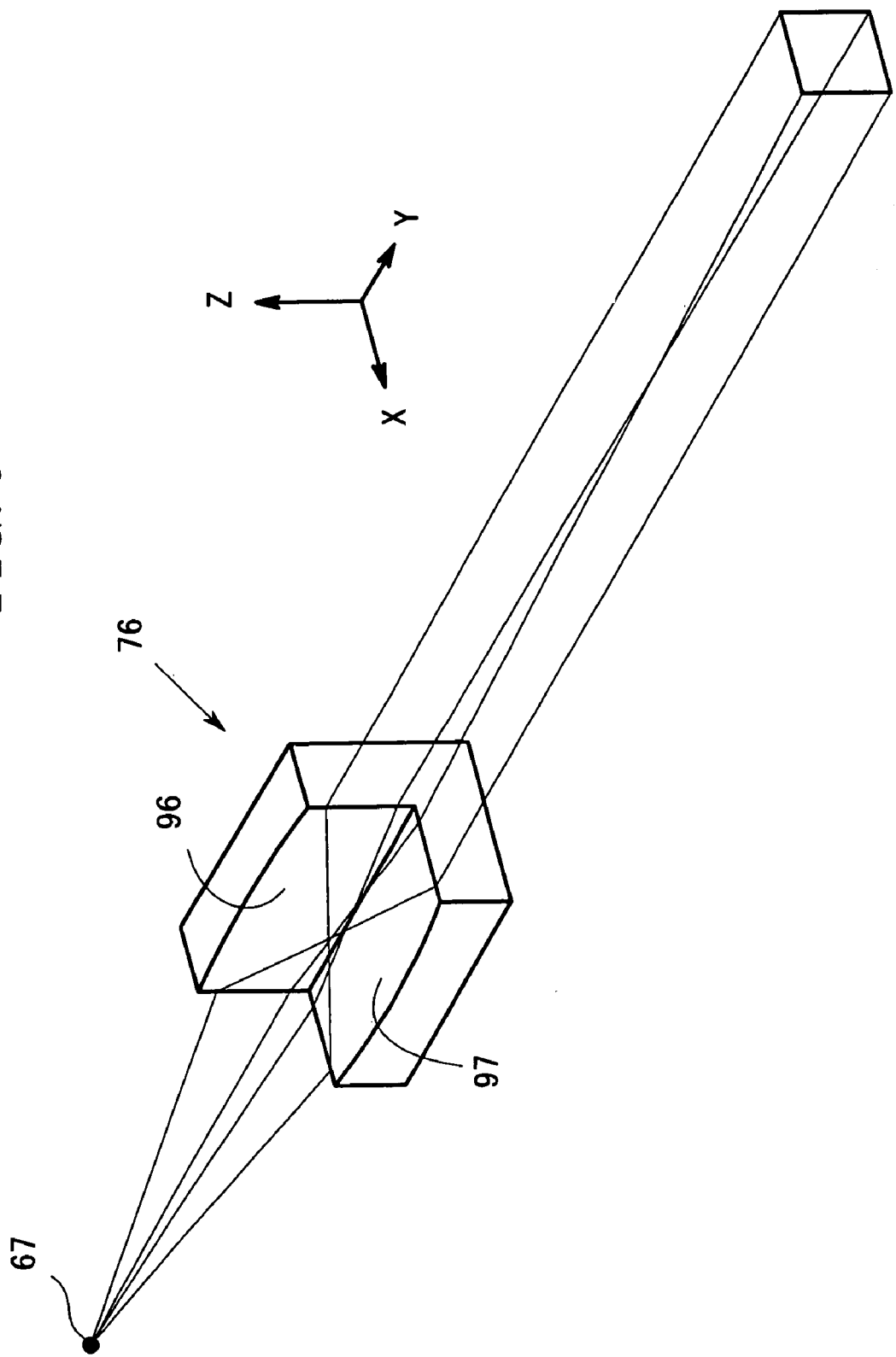
FIG. 6 is a perspective view of a multilayer-film mirror.

The multilayer-film mirror 76 includes, as shown in FIG. 6, a first mirror having a first parabolic reflection surface 96 made of synthetic multilayer films and a second mirror having a second parabolic reflection surface 97 made of synthetic multilayer films so as to form a multilayer-film mirror having a so-called side-by-side structure in that the first and second mirrors are joined to each other at their sides at an angle of about 90°. Using the multilayer-film mirror 76, an X-ray beam (diverging beam) emitted from an X-ray focus 67 of the X-ray tube 66 can be collimated within the X-Y plane as well as within the Y-Z plane. An X-ray reflected at the first reflection surface 96 at first is further reflected at the second reflection surface 97 and goes out. On the other hand, an X-ray reflected at the second reflection surface 97 at first is further reflected at the first reflection surface 96 and goes out. The first reflection surface 96 collimates the X-ray in the X-Y plane while the second reflection surface 97 collimates the X-ray in the Y-Z plane. The X-ray beam diverging from the X-ray focus 67 is collected on the parabolic surface and collimated, so that a parallel beam can be obtained with a high intensity. Using this multilayer-film mirror, a divergence angle of an X-ray can be reduced within a range of 0.04°, for example. If the collimation is insufficient with the use of the multilayer-film mirror only, the incident monochromator device may be used, as will be described later.

Referring back to FIG. 2, the incident-monochromator device 70 includes a plurality of monochromators therein, and these monochromators can be switched for use. FIG. 5 shows a state in that a four-crystal monochromator 78 is used. Using the incident-monochromator device 70, an incident X-ray is made monochromatic in addition to the collimation, enabling X-ray diffraction to be measured with a high resolution.

Figure 7:
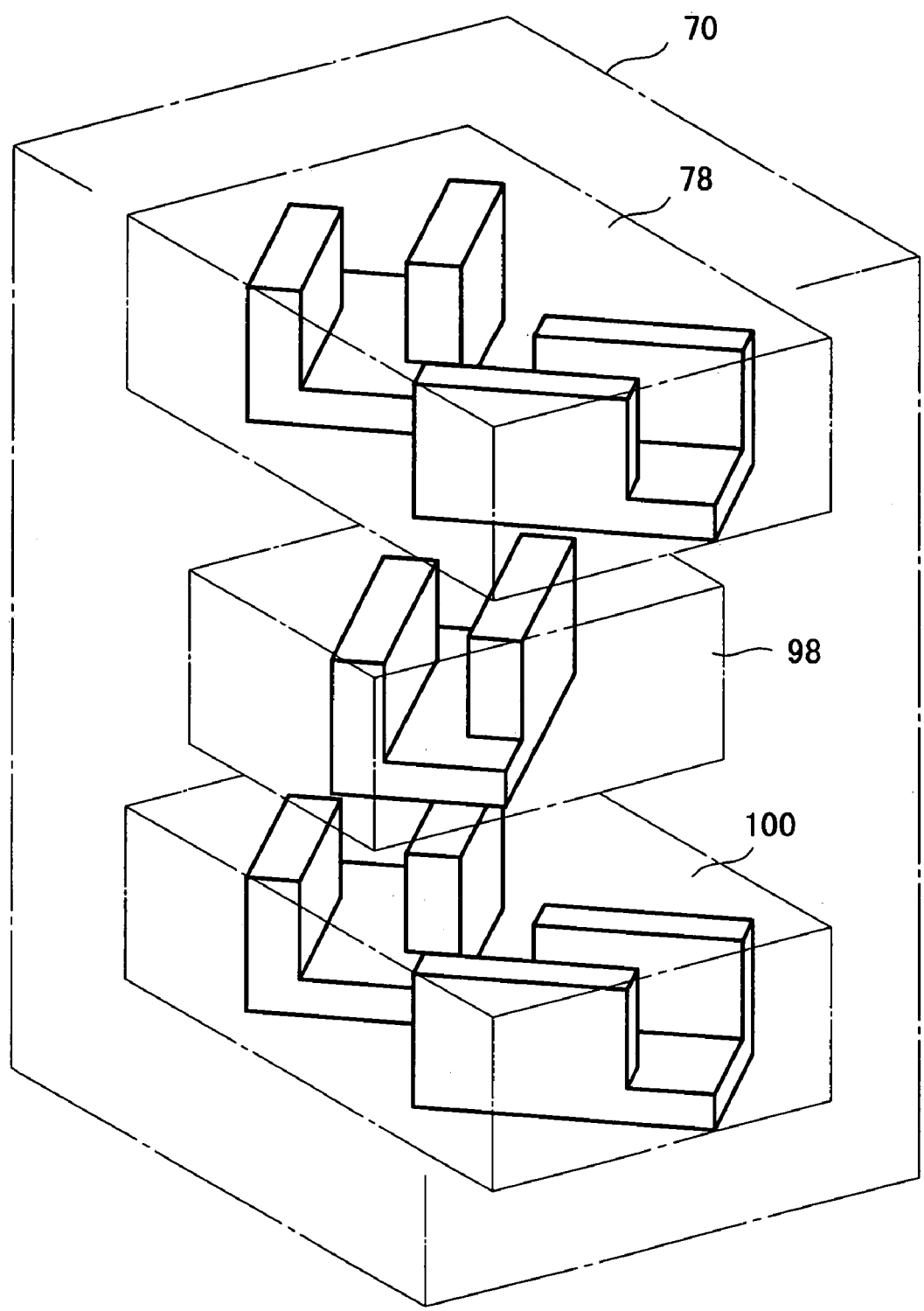
FIG. 7 is a perspective view schematically showing the inside of an incident-monochromator device.

FIG. 7 is a perspective view of the incident-monochromator device 70, schematically showing the inside thereof, in which three kinds of monochromators are arranged in the vertical direction: the four-crystal monochromator 78 using combined two channel-cut crystals which uses a Ge (220) plane as a reflection surface, the full width at half maximum (FWHM) of a reflection peak being 12 seconds in angle; a monochromator 98 using one channel-cut crystal which uses a Si(400) plane as a reflection surface and uses four-times reflection, the FWHM of the reflection peak being 3.6 seconds in angle; and a four-crystal monochromator 100 using combined two channel-cut crystals which uses a Si(220) plane as a reflection surface, the FWHM of the reflection peak being 5.5 seconds in angle. A vertical movement of these monochromators allows a desired monochromator to be inserted into an optical path of an X-ray.

Figure 8A:
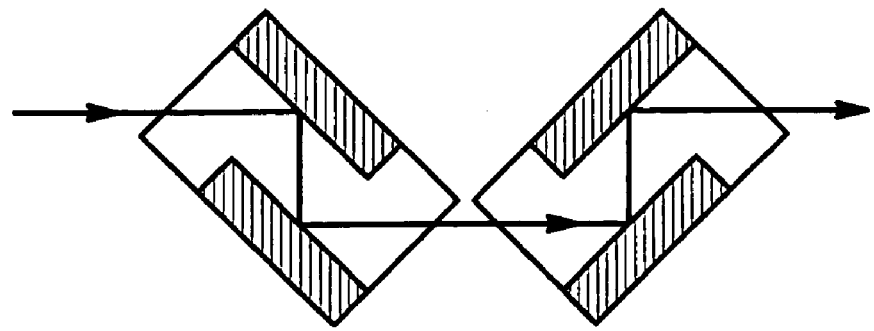
FIGS. 8A, 8B and 8C are plan views showing functions of a four-crystal monochromator using two channel-cut crystals, a monochromator using one channel-cut crystal, and a Soller slit, respectively.
Figure 8B:
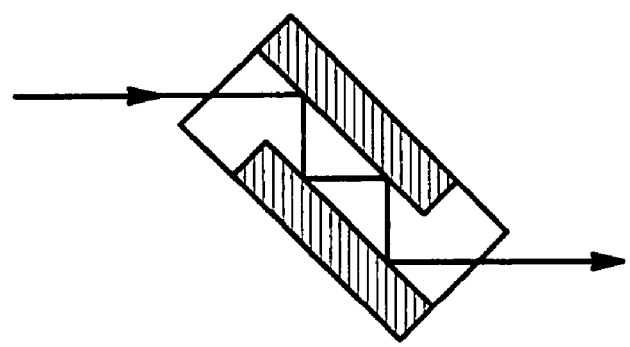

FIG. 8A is a plan view showing a function of the four-crystal monochromator using combined two channel-cut crystals and FIG. 8B is a plan view showing a function of four times reflection of a monochromator using one channel-cut crystal.

Figure 9:
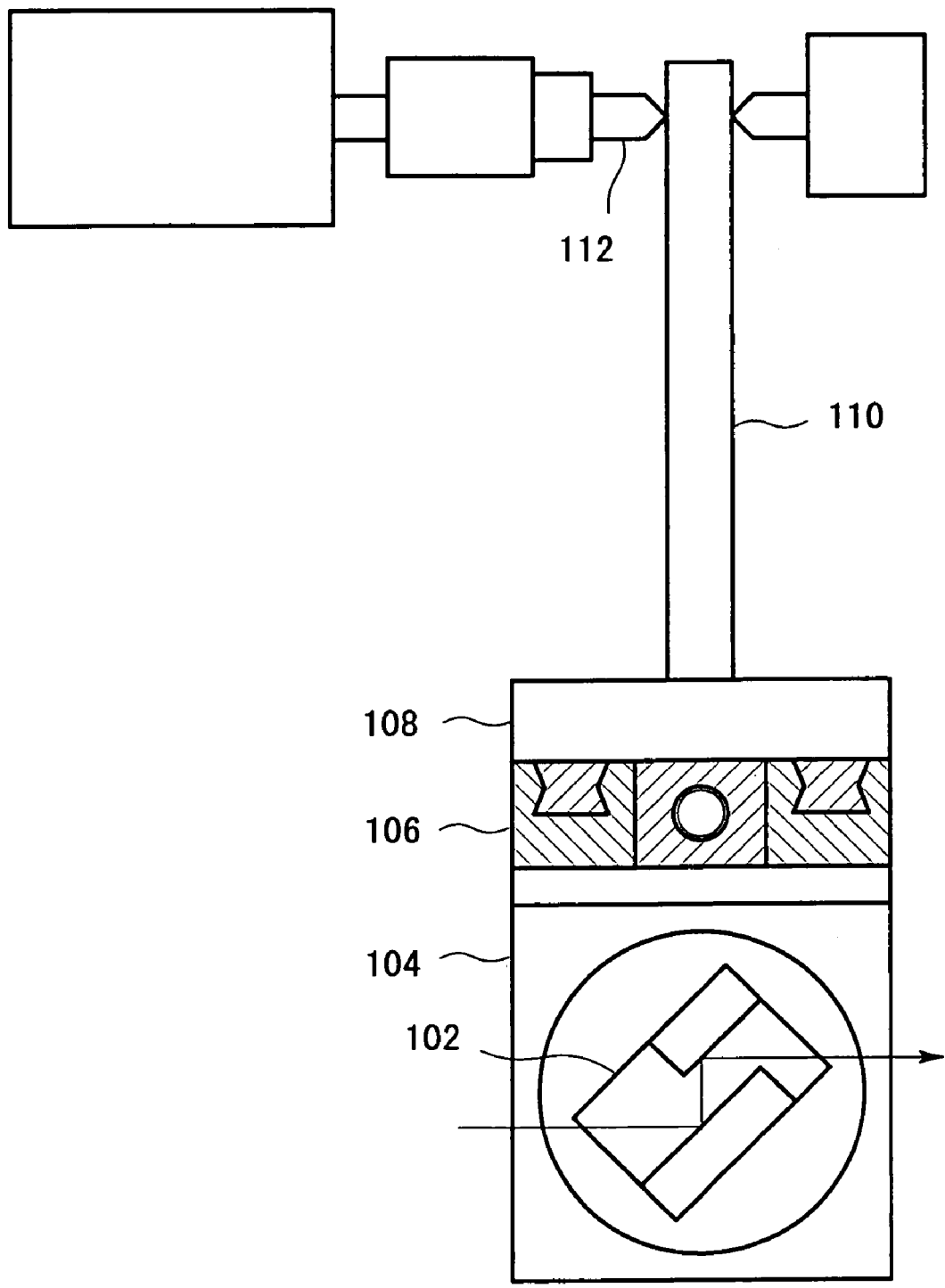
FIG. 9 is a plan view of a fine adjustment mechanism having a sine-bar.

When any monochromator is switched, with a vertical movement, to the position in use, only a slight degree of the positional adjustment is made with a sine-bar system after the switching. FIG. 9 is a plan view of a fine adjustment mechanism concerning the rear channel-cut crystal 102 of the four-crystal monochromator 78 which is composed of a front channel-cut crystal and a rear channel-cut crystal as shown in FIG. 7. The rear channel-cut crystal 102 is mounted on a crystal support table 104, which is fixed to an elevating mechanism 106 that is movable up and down along an elevating guide 108. A sine-bar 110 has a root which is fixed to the elevating guide 108, which can turn by a very small angle. An end of the sine-bar 110 is pushed by a pushrod 112, so that the rotation of the elevating guide 108 allows the crystal support table 104 to turn, resulting in the fine adjustment of a rotational angle of the rear channel-cut crystal 102 so as to take out an X-ray beam properly. Assuming that the length of the sine-bar 110 is 100 mm, for example, the adjustment is possible with an angular accuracy not more than $1/10{,}000°$.

The front channel-cut crystal of the four-crystal monochromator 78 shown in FIG. 7 is also provided with a fine adjustment system having the sine-bar system in the same way as in the above-mentioned rear channel-cut crystal 102. It is noted that two channel-cut crystals of the other four-crystal monochromator 100 and a channel-cut crystal of the channel-cut monochromator 98 are provided with the same fine adjustment mechanism having the sine-bar system.

Assuming that the position at which the X-ray enters the incident-monochromator device 70 does not vary, when the four-crystal monochromator is switched to the channel-cut monochromator (or vice versa), the position at which the X-ray goes out of the incident-monochromator device 70 is changed inconveniently. Then, according to the embodiment, in order to keep the same position of the X-ray going out of the incident-monochromator device 70, the X-ray tube 66 and the multilayer-film mirror device 68 can be shifted in the X-direction in FIG. 2, depending on the selection of the four-crystal monochromator or the channel-cut monochromator in the incident-monochromator device 70. Alternatively, the X-ray tube 66 and the multilayer-film mirror device 68 may be left as they are, while the sample support mechanism 24 and the receiving optical system 26, which are shown in FIG. 2, may be shifted in the X-direction depending on the position of the X-ray going out of the incident-monochromator device 70.

Next, a receiving optical system will be described. Referring to FIGS. 2 and 5, the receiving optical system 26 includes a receiving slit device 80, an analyzer device 82, and an X-ray detector 84. The analyzer device 82 has two kinds of channel-cut analyzer crystals and one Soller slit therein so that they can be switched for use. FIG. 5 shows a state in that a channel-cut analyzer crystal 86 is used.

Figure 8C:
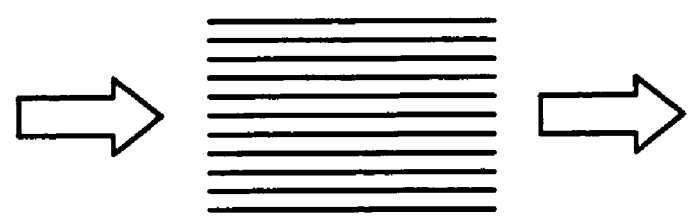
Figure 10:
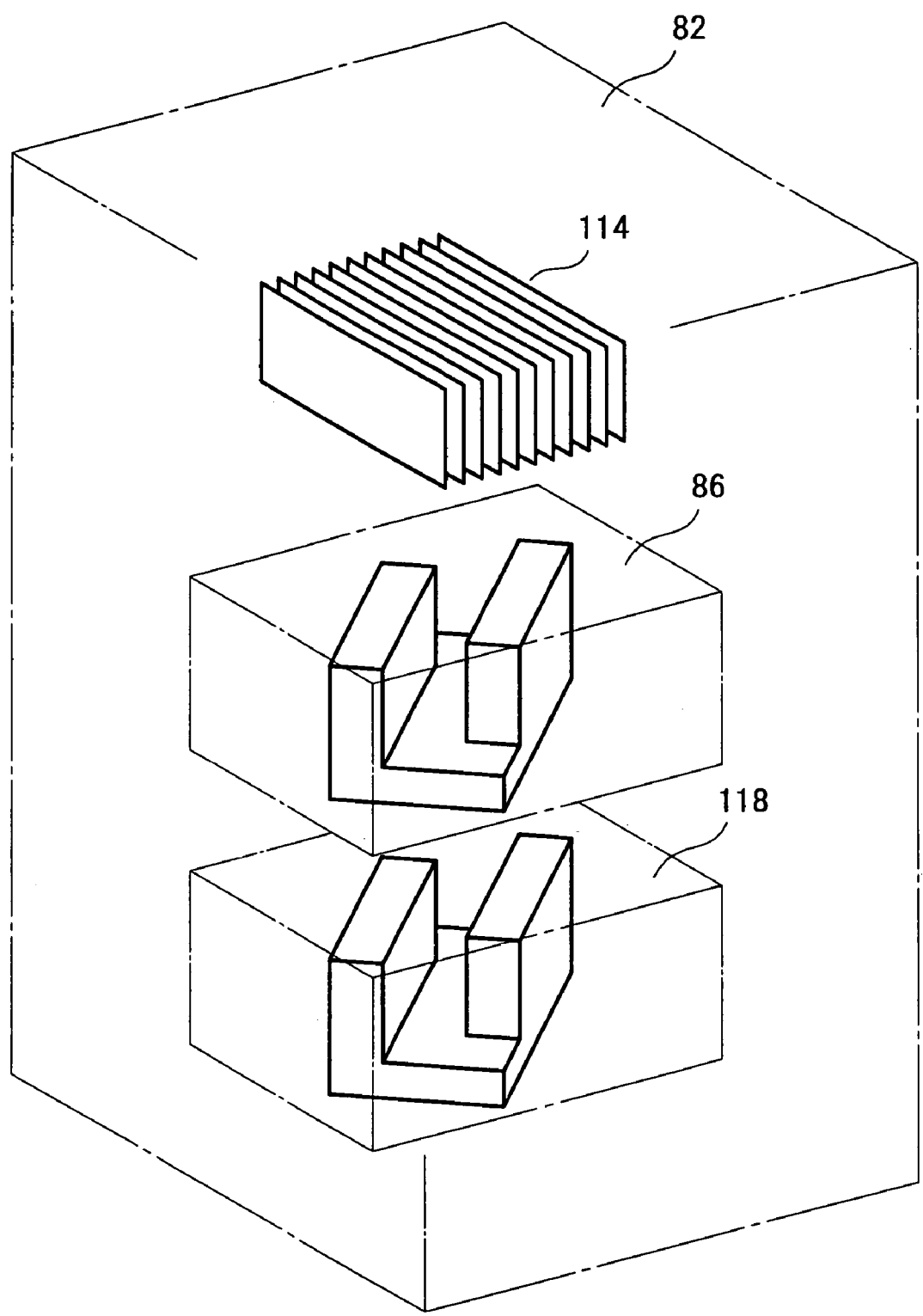
FIG. 10 is a perspective view schematically showing the inside of an analyzer device.

FIG. 10 is a perspective view of the analyzer device 82 schematically showing the inside thereof in that there are three kinds of components: explaining from above, a Soller slit 114; the channel-cut analyzer crystal 86 using a Si(400) plane as a reflection surface and using four-times reflection, the FWHM of the reflection peak being 3.6 seconds in angle; and a channel-cut analyzer crystal 118 using a Ge(220) plane as a reflection surface and using four-times reflection, the FWHM of the reflection peak being 12 seconds in angle. A vertical movement of these components allows desired analyzer crystals or Soller slit to be inserted into an X-ray optical path. The inserted analyzer crystal is adjustable with the above-mentioned sine-bar system. The four-times reflection at the analyzer crystal is shown in FIG. 8B. FIG. 8C is a plan view of the Soller slit, which makes collimation within 0.1° in divergence angle, for example. Explaining how to use the analyzer device 82, the Soller slit 114 may be selected for the intensity-preferred case, while any one of the analyzer crystals may be selected for the resolution-preferred case such as making a reciprocal map.

Referring back to FIG. 2, the X-ray detector 84 is a scintillation counter, which can be moved, as shown in FIG. 5, in a direction perpendicular to the optical axis of the receiving optical system 26 along a guide 88. When the analyzer crystal 86 is switched to the Soller slit 114 in the analyzer device 82, the position at which an X-ray beam goes out must be shifted, that is, the X-ray detector 84 must be shifted in a direction denoted by an arrow 90 in FIG. 5.

Referring to FIG. 2, the receiving slit device 80, the analyzer device 82, and the X-ray detector 84 are mounted on a detector support table 92, which is supported by an upright circular-arc guide 94 and is rotatable along the guide 94 within a predetermined angular range within a vertical plane. The axis of rotation of the detector support table 92 is parallel to the X-direction and passes through the center of the sample surface. When the curved guide 36 is adjusted at the position shown in FIG. 2, the axis of rotation of the detector support table 92 coincides with the axis of rotation 37 of the attitude-change table 40. This rotation will be referred to as a counter-χ rotation. When the sample 60 is horizontal (the state for the in-plane diffraction measurement) and the optical axis of the incident optical system 22 and the optical axis of the receiving optical system 26 lie on one straight line, the axis of rotation 37 of the χ rotation of the sample 60 coincides with the axis of rotation of the counter-χ rotation of the receiving optical system 26.

The upright guide 94 is fixed to an end of a horizontal arm 120, whose root is fixed to the receiving-optical-system turntable 30. The 2θ rotation of the receiving-optical-system turntable 30 allows the entire receiving optical system 26 to turn by 2θ.

Specification values of the various movements of the X-ray diffraction apparatus are listed as follows:

ω rotation: −95° to +185°, 0.0001° in resolution, encoder control;

2θ rotation: −160° to +160°, 0.0001° in resolution, encoder control;

χ rotation: +92° to −5°, 0.001° in resolution;

counter-χ rotation: −2° to +12°, 0.001° in resolution;

U- and V-movements: 100 mm in stroke, 0.001 mm in resolution;

W-movement: −20 mm to +1 mm, 0.0005 mm in resolution;

Ru and Rv rotations: −3° to +3°, 0.001° in resolution; and

φ rotation: −185° to +185°, 0.0001° in resolution, full-closed encoder control.

Figure 12:
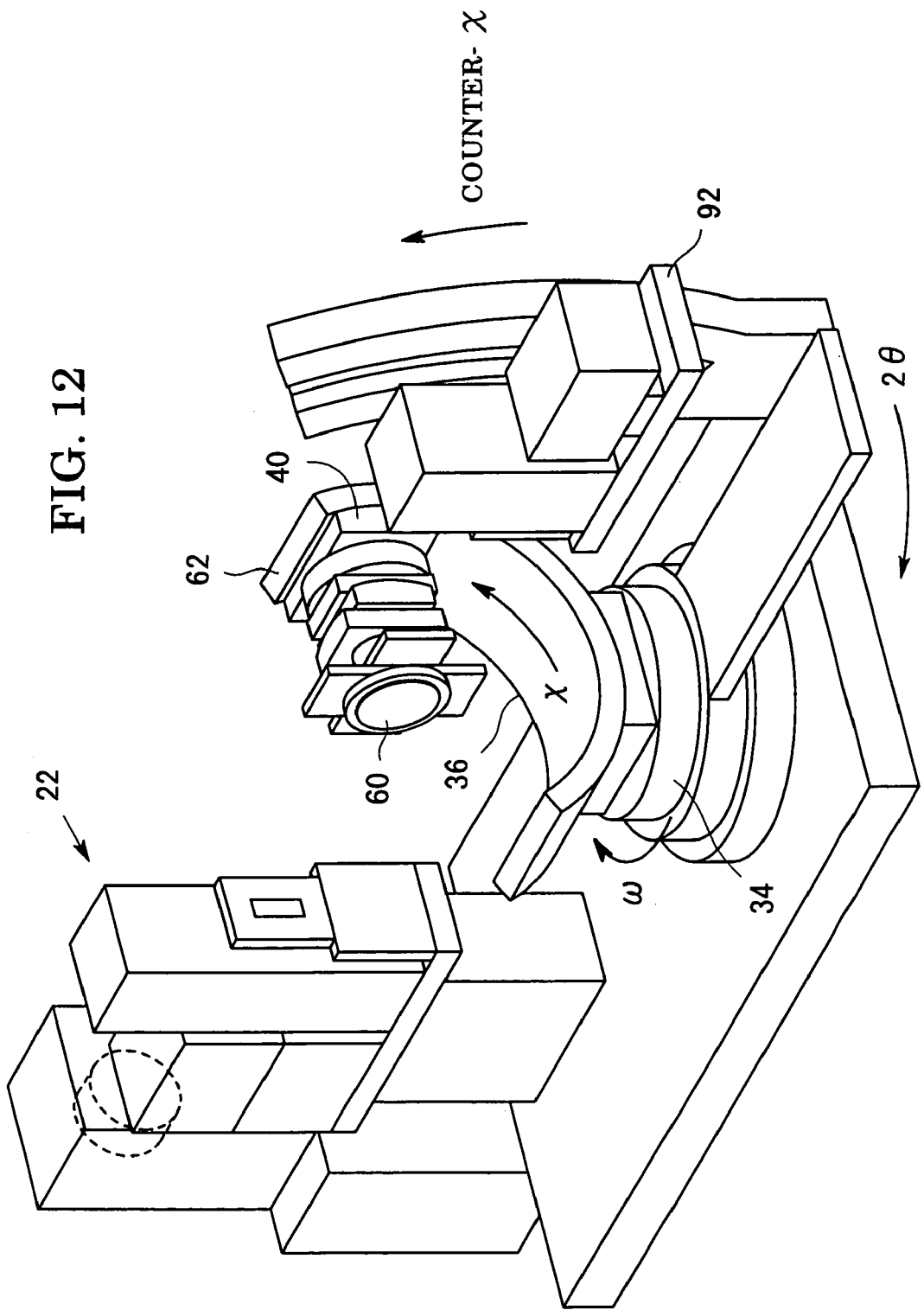
FIG. 12 is a perspective view showing a process for switching the X-ray diffraction apparatus shown in FIG. 2 into a mode of the out-of-plane diffraction measurement.

It is noted that in the specification values mentioned above: the origin of the ω rotation is located at the position shown in FIG. 12 and the clockwise direction viewed from above is defined as positive; the origin of the 2θ rotation is located at the position shown in FIG. 12 and the clockwise direction viewed from above is defined as positive; the origin of the χ rotation is located at the position shown in FIG. 12 and the counterclockwise direction viewed from the incident optical system 22 is defined as positive; the origin of the counter-χ rotation is located at the position (the detector support table 92 is in a horizontal state) shown in FIG. 12 and the upward rotation is defined as positive; the origin of the W-movement is located at the position at which the surface of the sample table 58 is located at the X-ray irradiation position in FIG. 3 and the direction in which the sample table 58 goes away from the attitude-change table 40 is defined as positive; the origin of the Ru and Rv rotations is located at the position shown in FIG. 3; and the origin of the φ rotation is located at the position shown in FIG. 3.

Next, an operation of the X-ray diffraction apparatus will be described. The in-plane diffraction measurement of a thin-film sample is described at first. The sample support mechanism 24 is adjusted to the attitude shown in FIG. 2. That is, the surface of the sample 60 becomes substantially horizontal. Then, the one end 62 of the curved guide 36, in the vicinity of which the through-hole 63 has been formed, is directed to the incident X-ray. When the curved guide 36 is located at such a position, the angle of the surface of the sample 60, in FIG. 3, relative to the X-ray incident direction which remains unchanged, i.e., the incident angle α shown in FIG. 1A, can be controlled by rotating the attitude-change table 40 along the curved guide 36 by a very small angle in the χ rotation (see FIG. 4).

During the in-plane diffraction measurement, the sample turntable 42 is rotated in the φ rotation (see FIG. 4) so as to rotate the sample 60 in the in-plane rotation. If the sample surface is not perpendicular to the axis of rotation 45 of the φ rotation, the sample surface is to undulate. In order to prevent the undulation, the first adjustment table 48 and the second adjustment table 50 are adjusted precisely in the Ru and Rv rotations respectively, so that the axis of rotation (which is identical with the normal line 61 of the sample surface) of the elevating pedestal 52 can coincides with the axis of rotation 45 of the φ rotation.

Referring to FIG. 5, the X-ray emitted from the rotating anode target 74 is reflected by the multilayer-film mirror 76 to be collimated. The X-ray is further reflected by the four-crystal monochromator 78 to be further collimated and made monochromatic, and then passes through the incident-slit device 72 and further through the through-hole 63 of the curved guide 36 to be incident on the sample 60.

Figure 11:
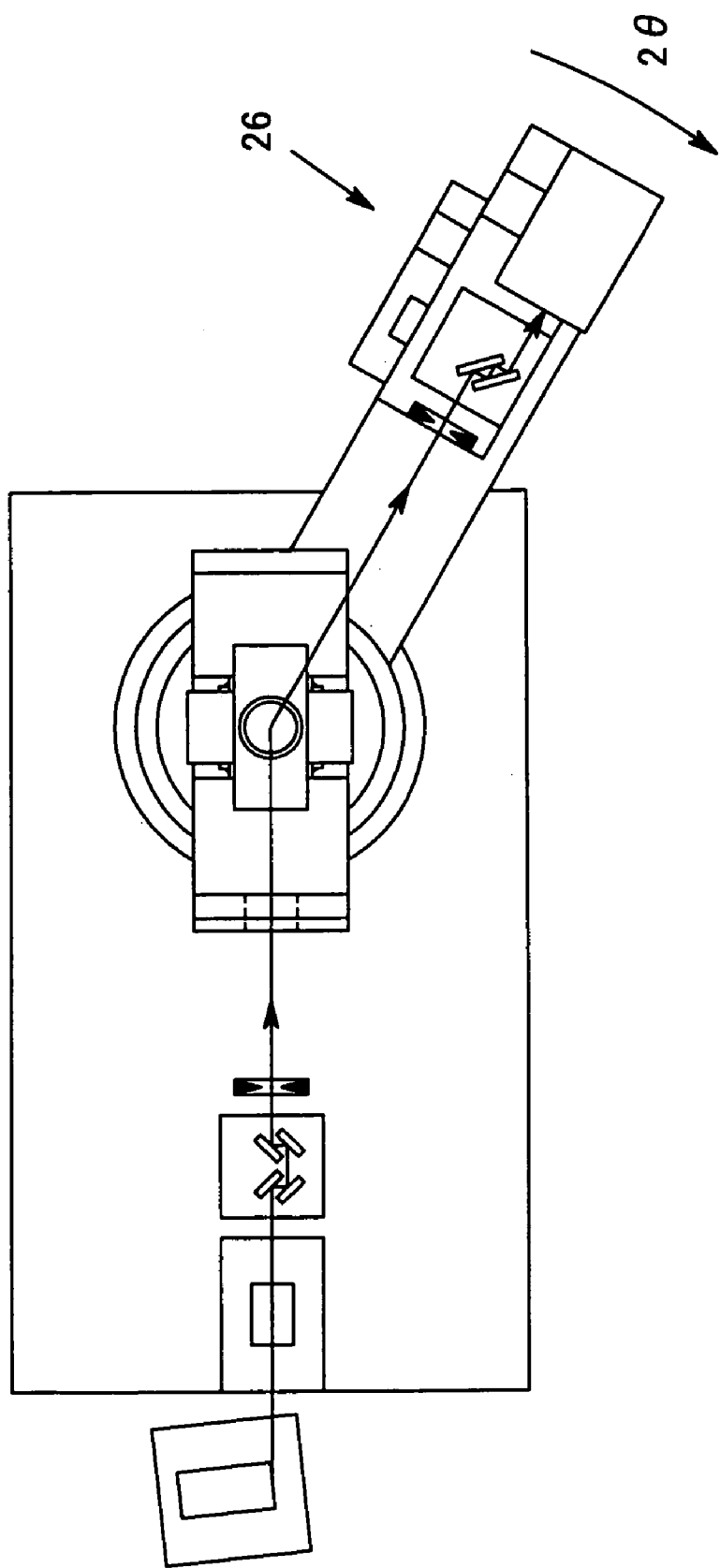
FIG. 11 is a plan view showing a state in the in-plane diffraction measurement using the X-ray diffraction apparatus shown in FIG. 5.

After the state mentioned above is attained, the receiving optical system 26 is rotated in the 2θ rotation from the state shown in FIG. 5 to the sate of FIG. 11, so that the diffracted X-ray is measured within a plane substantially flush with the sample surface, enabling the in-plane diffraction to be measured. In this case, the direction of the lattice plane of the sample is adjusted with the φ rotation if necessary.

Figure 1A:
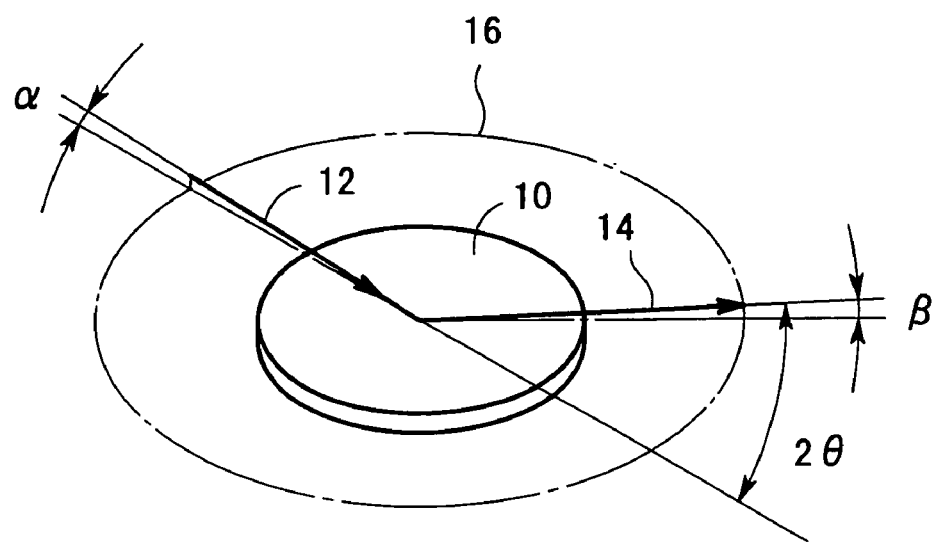
FIGS. 1A and 1B are perspective views illustrating in-plane diffraction measurement and out-of-plane diffraction measurement, respectively.

In this case, the detector support table 92 shown in FIG. 2 has been rotated by a very small angle in the χ rotation, so that the outgoing angle β shown in FIG. 1A has been set at a desired value, about 0.1 to 0.5°, for example. Furthermore, the angle in the counter-χ rotation can be changed so that the in-plane diffraction measurement can be made for various outgoing angles β. When the in-plane diffraction is measured with the change of the outgoing angle β, the variation of the crystal information of the sample surface in the depth direction can be obtained. Also, the counter-χ rotation enables the reflectance measurement to be made in the vertical direction, required before the in-plane diffraction measurement.

Figure 13:
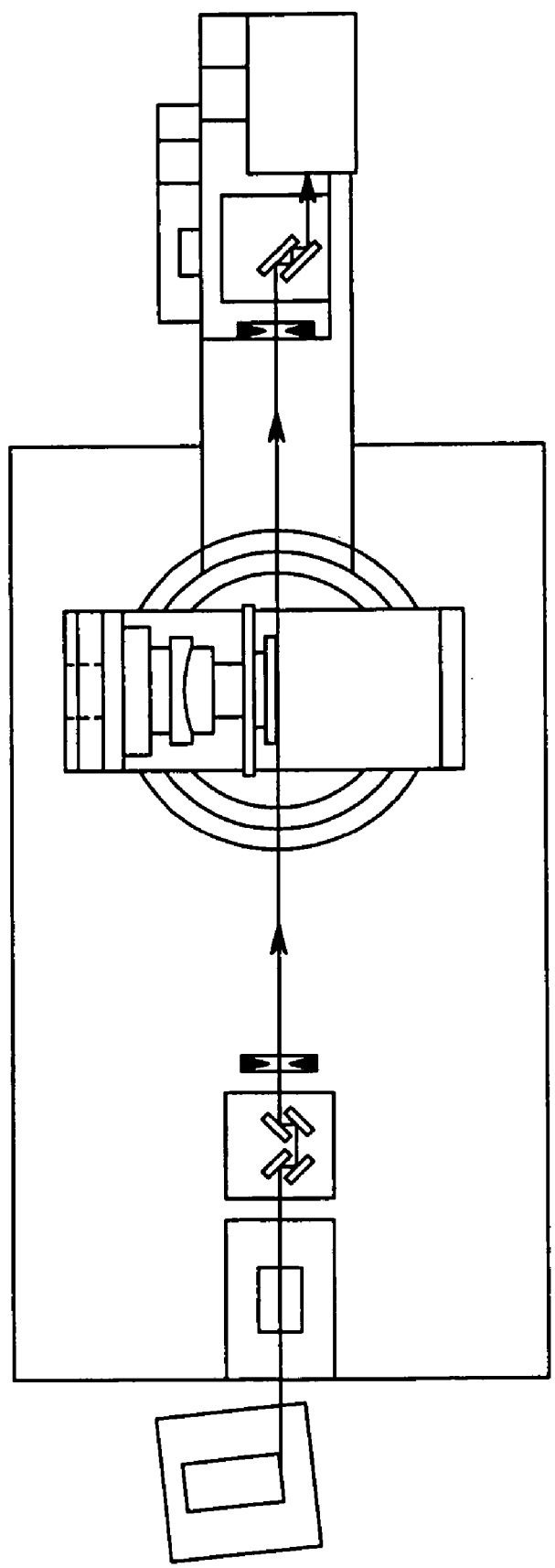
FIG. 13 is a plan view of the X-ray diffraction apparatus in the mode shown in FIG. 12.

Next, a method for switching from the in-plane diffraction measurement to the out-of-plane diffraction measurement will be described. First, as shown in FIG. 12, the curved-guide turntable 34 is co-rotated clockwise by 90° from the state shown in FIG. 2, so that the direction of the curved guide 36 is changed. Then, the attitude-change table 40 is χ-rotated along the internal surface of the curved guide 36 to move to the vicinity of the one end 62 of the curved guide 36, so that the surface of the sample 60 becomes upright. FIG. 13 is a plan view of the state shown in FIG. 12.

Figure 14:
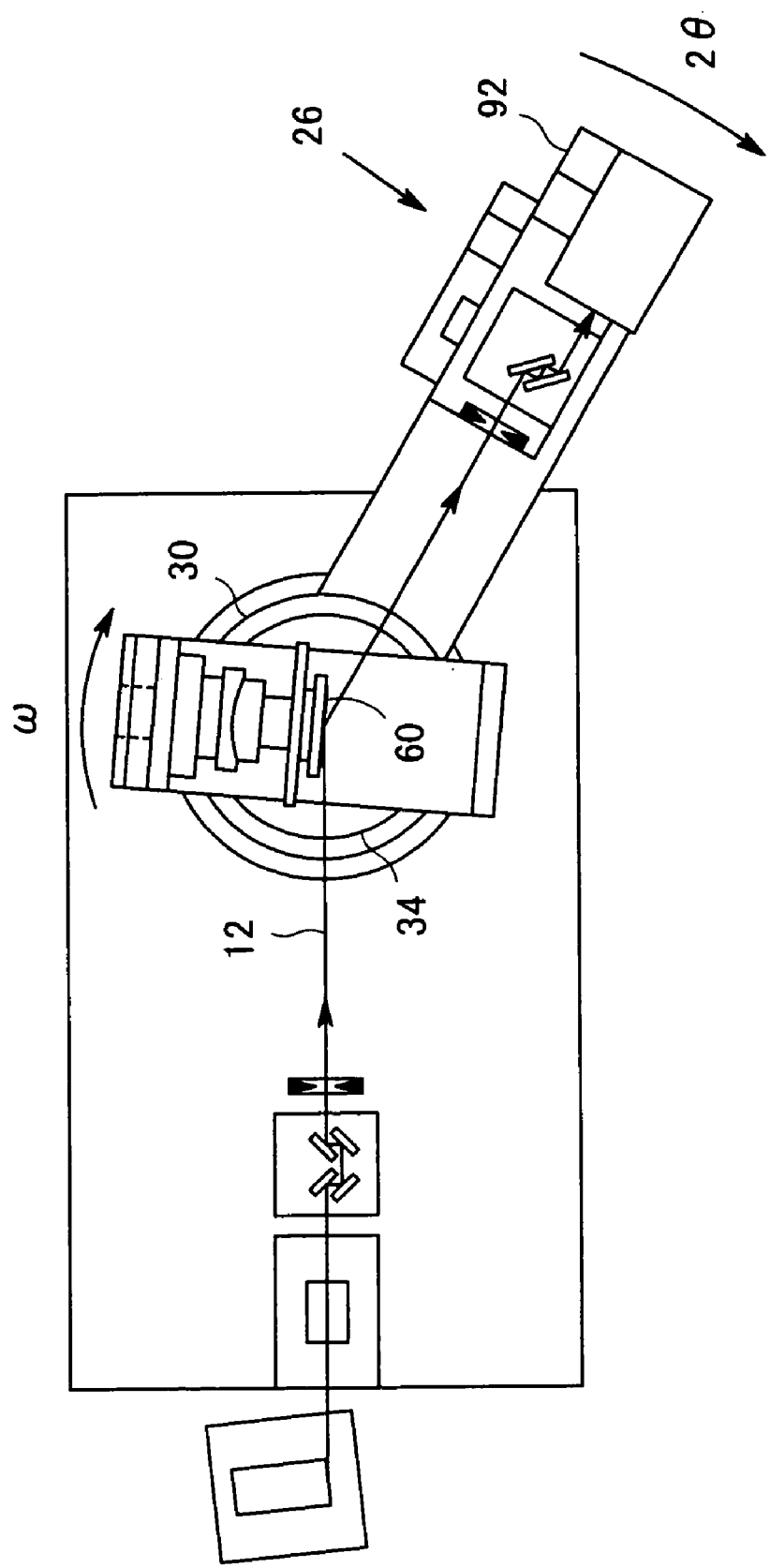
FIG. 14 is a plan view showing a state in the out-of-plane diffraction measurement using the X-ray diffraction apparatus shown in FIG. 13.

Next, as shown in FIG. 14, an incident angle of an X-ray 12 on the surface of the sample 60 is adjusted by the ω rotation of the curved-guide turntable 34 with a required angle, with the detector support table 92 being held horizontal. Then, for example, while the curved-guide turntable 34 is ω-rotated, the receiving-optical-system turntable 30 is rotated at the double angular speed (so-called θ–2θ scanning), so that a diffraction pattern can be measured, resulting in the out-of-plane diffraction measurement. Further, in the state shown in FIG. 14, in order to measure a thin film, a so-called asymmetrical measurement can be executed in a manner that while the incident angle is fixed at a very small angle α, only the receiving-optical-system turntable 30 is rotated.

As described above, according to the X-ray diffraction apparatus, the diffraction plane which must have a high degree of resolution does exist in the horizontal plane in both the in-plane diffraction measurement and the out-of-plane diffraction measurement. In the diffraction plane, the following operations are made: (1) an incident X-ray is collimated by the first reflection surface 96 of the multilayer-film mirror 76; (2) the incident X-ray is further collimated and monochromated by the four-crystal monochromator or the channel-cut monochromator in the incident-monochromator device 70; (3) when the channel-cut analyzer crystal is used in the analyzer device 82, the diffracted X-ray is collimated by this analyzer crystal; and (4) in the receiving optical system 26, the 2θ rotation control is executed with a high degree of accuracy. With these operations, both the in-plane diffraction measurement and the out-of-plane diffraction measurement can be performed with a high degree of resolution.

Figure 1B:
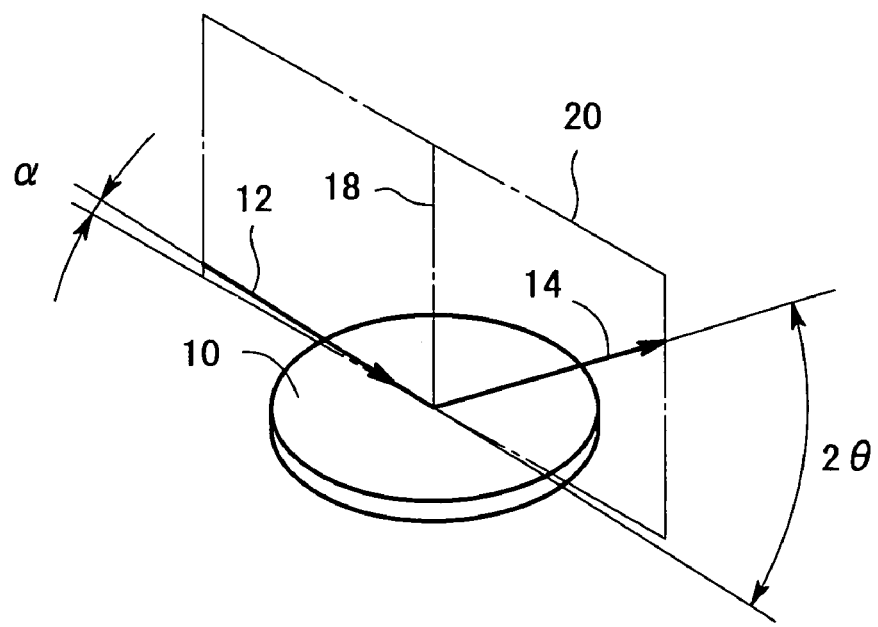

Since the multilayer-film mirror 76 shown in FIG. 6 is used according to the embodiment, an X-ray is collimated not only within the diffraction plane (the X-Y plane) but also within the Y-Z plane perpendicular thereto. When the X-ray is collimated within the Y-Z plane, the divergence in the direction of the incident angle α shown in FIGS. 1A and 1B is reduced, improving the accuracy of the in-plane diffraction measurement.

Figure 15:
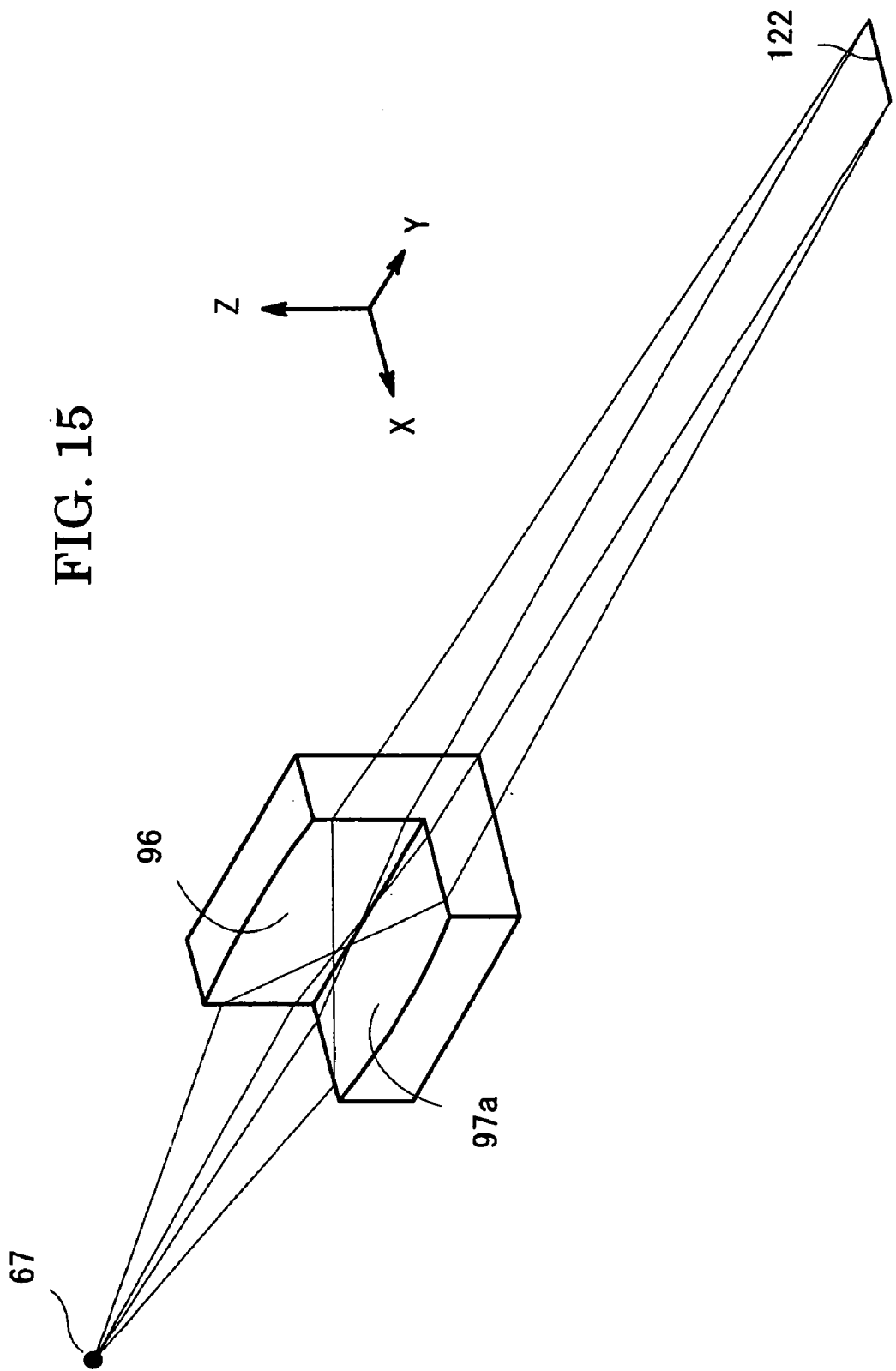
FIG. 15 is a perspective view of a modification of the multilayer-film mirror.

Next, another embodiment will be described. The embodiment described above uses the multilayer-film mirror having two parabolic reflection surfaces. Alternatively, a second reflection surface 97a may be of an elliptic arc shape as shown in FIG. 15, the first reflection surface 96 being of the parabolic shape as it is. An X-ray becomes a focusing beam within the Y-Z plane to converge on the sample surface while the X-ray becomes a collimated beam within the X-Y plane. For example, when a focus 67 of an X-ray is a point focus with a diameter of 0.07 mm, the X-ray becomes a converging ray 122 with a cross-sectional area of 1 mm×0.2 mm in the vicinity of the sample, so that the X-ray intensity on the sample surface can be increased. When the intensity-preferred measurement is desired, a multilayer-film mirror of the type shown in FIG. 15 may be used. Even in this case, since the X-ray is collimated as it is within the X-Y plane, the collimation of an X-ray beam in the direction of the 2θ rotation is maintained (diverging angle is less than 0.04°, for example), so that the resolution in the 2θ rotation (i.e., the resolution of the diffraction angle) is maintained high.

In the case of using the multilayer-film mirror of the type shown in FIG. 15, if the resolution in the depth direction of the sample is preferred rather than the intensity, the opening width in the vertical direction of the incident-slit device 72 may be restricted for reducing the divergence of the incident angle α.

Figure 16:
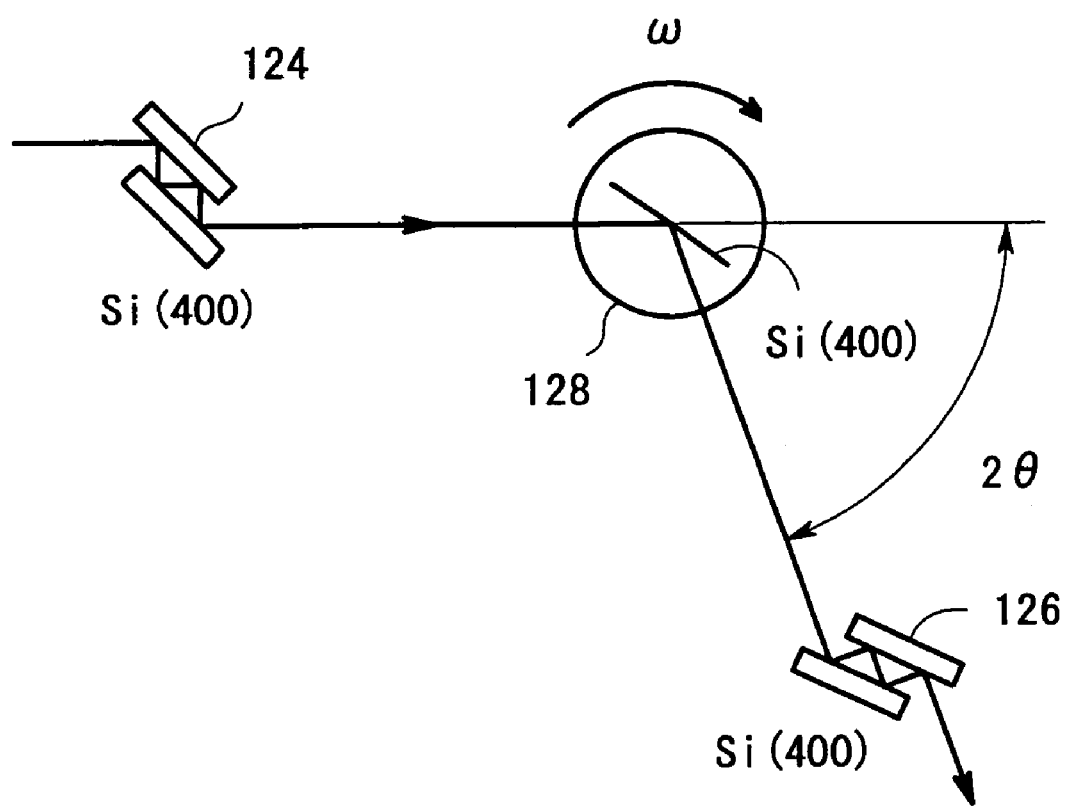
FIG. 16 is a layout drawing of a monochromator, an analyzer crystal and a sample in a measurement example 1.

Next, measurement examples using the X-ray diffraction apparatus shown in FIG. 2 will be described. A measurement example 1 is for verifying the angular resolution of the apparatus. FIG. 16 is a plan view of the measurement condition showing a monochromator selected in the incident monochromator device, a monochromator selected in the analyzer device and a sample. In the incident-monochromator device, a channel-cut monochromator 124 using a Si(400) plane and four-times reflection was selected, and in the analyzer device, a channel-cut analyzer crystal 126 using the same Si(400) plane and four-times reflection was also selected likewise. The sample was a single crystal Si wafer 128 which was used as a standard sample. The surface of the wafer 128 was parallel to the Si(100) plane. The in-plane diffraction of this sample was measured so as to detect the diffracted X-ray from the Si(400) plane.

FIG. 17 is a graph showing measured results of the measurement example 1. An X-ray peak intensity of the Si(400) diffraction is represented in contour. This graph was obtained in a manner as described below. Referring to FIG. 16, first, the 2θ was set at about 69.1° while the ω was brought to a position at which the Si(400) diffraction peak can be detected, defining that Δω is zero at this position. Next, diffracted X-ray intensities were measured for various combinations of 2θ and ω within a range of a very small angle. It is seen in FIG. 17 that a very sharp diffraction peak was obtained in the 2θ direction as well as in the ω direction, an angular resolution being about $1/1{,}000°$ or higher in any directions.

Figure 18A:
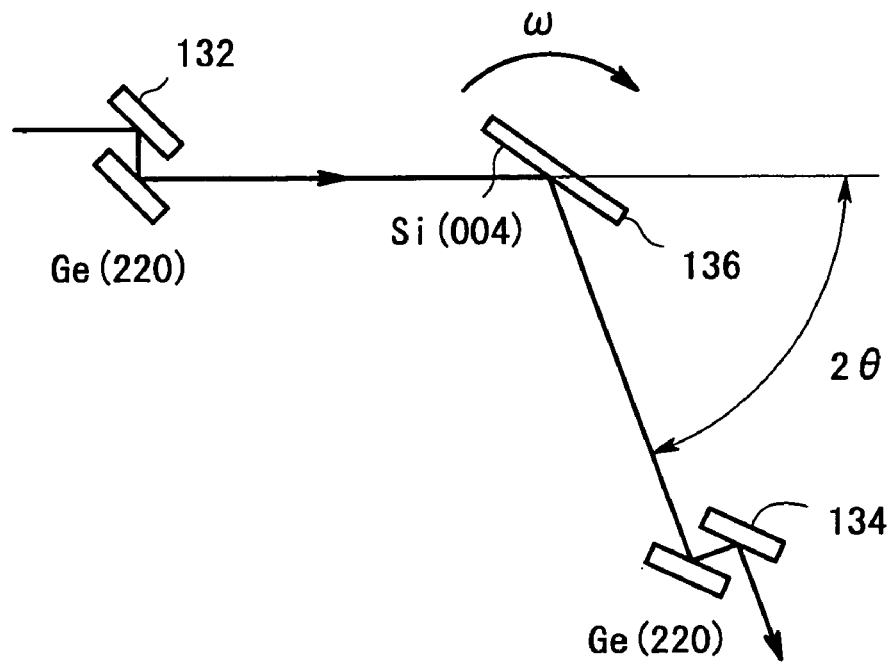
FIGS. 18A and 18B are layout drawings of a monochromator, an analyzer crystal and a sample in a measurement example 2.
Figure 18B:
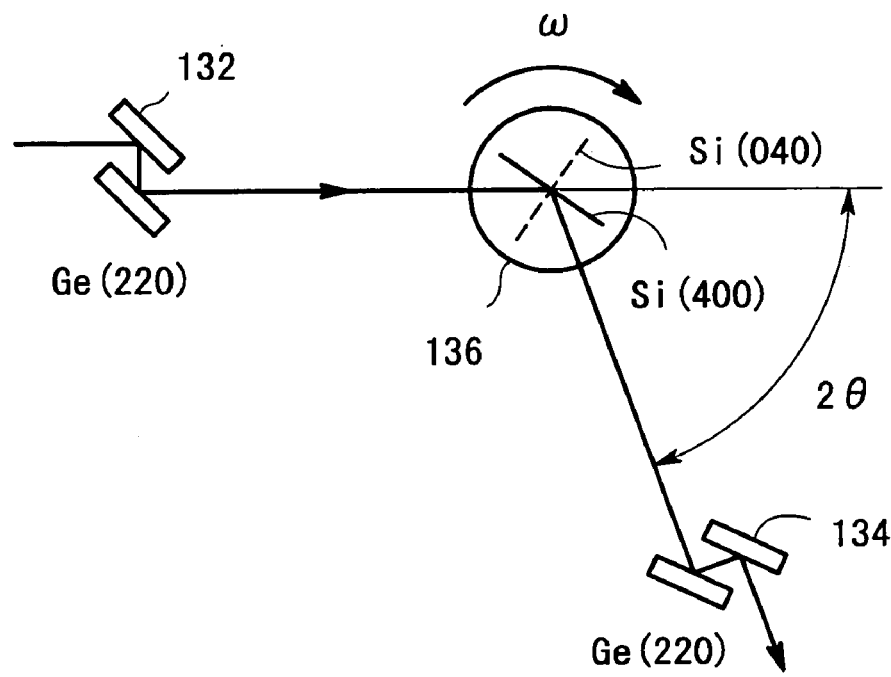

Next, a measurement example 2 will be described. A sample in the measurement example 2 was a single crystal silicon thin film deposited on a sapphire substrate. This sample is called as SOS (silicon on sapphire). The thickness of the silicon thin film was 100 nm. FIGS. 18A and 18B are plan views showing an arrangement of a monochromator, an analyzer crystal and the sample in the measurement example 2, FIG. 18A showing the out-of-plane diffraction measurement while FIG. 18B showing the in-plane diffraction measurement. In both the cases, a channel-cut monochromator 132 using a Ge(220) plane and two-times reflection was selected in the incident-monochromator device, and a channel-cut analyzer crystal 134 using the same Ge(220) plane was selected in the analyzer device too. In the out-of-plane diffraction measurement shown in FIG. 18A, a sample 136 was set upright, and the diffracted X-ray was measured from a Si(004) plane parallel to the thin film surface. On the other hand, in the in-plane diffraction measurement shown in FIG. 18B, the sample 136 was set horizontal, and the diffracted X-ray was measured from the Si(400) plane and a Si(040) plane both of which are perpendicular to the thin film surface. The 2θ was about 69°.

Figure 19:
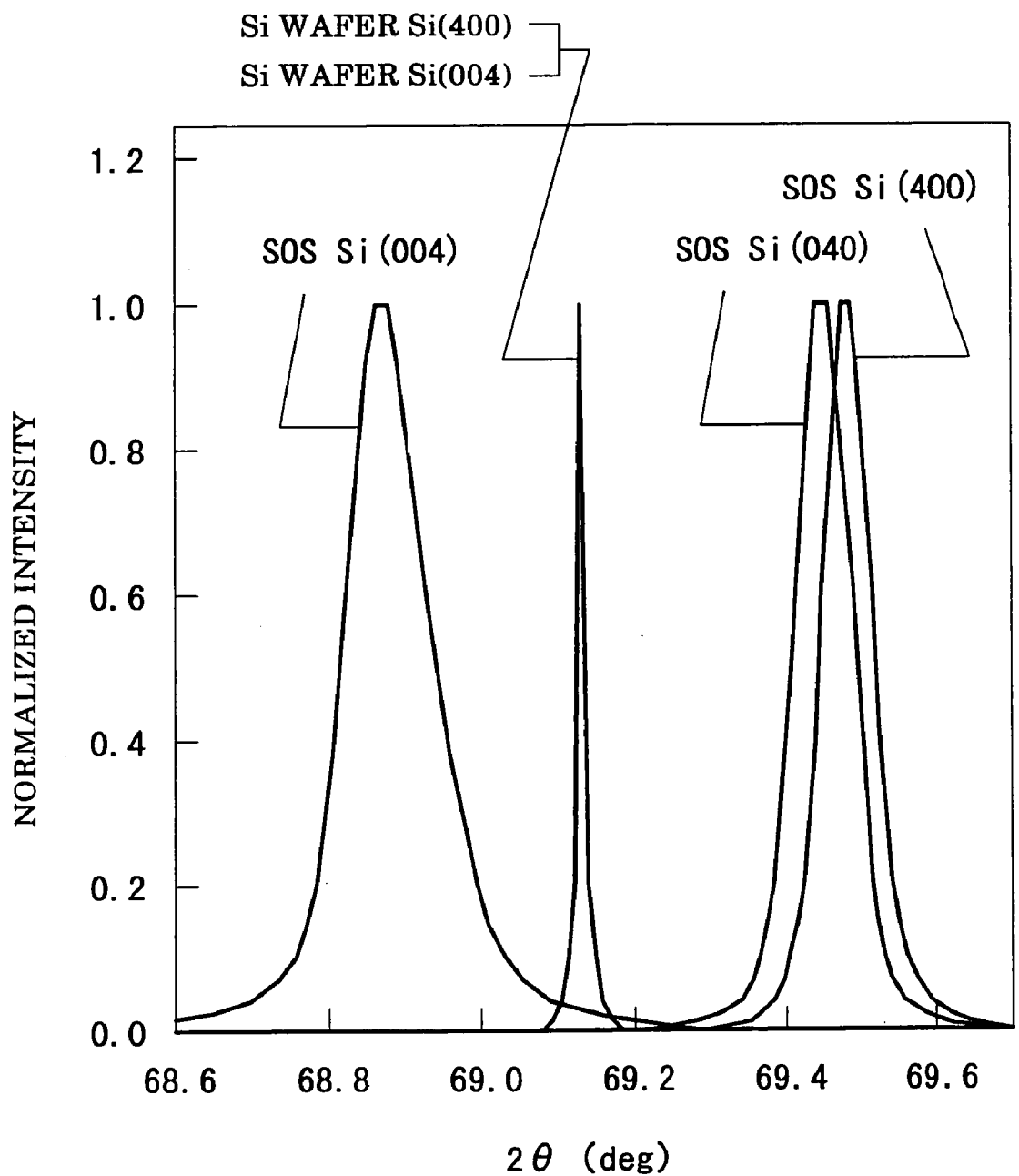
FIG. 19 is a graph of measured results in the measurement example 2.

FIG. 19 is a graph showing the measured results in the measurement example 2 mentioned above. A Si(004) diffraction peak of the SOS sample, obtained in the out-of-plane diffraction measurement, appears at about 68.9°, while Si(400) and Si(040) diffraction peaks of the SOS sample, obtained in the in-plane diffraction measurement, appear at about 69.5°. On the other hand, Si(400) and Si(004) diffraction peaks of a single crystal silicon wafer are shown for reference, these appearing at about 69.1°. Incidentally, the unit cell of the silicon crystal is cubic, so that if it is not strained, the lattice spacings of (400), (040), and (004) are identical to each other, the diffraction peaks being to appear at the same position. Accordingly, the measurement results shown in FIG. 19 is understood to indicate that a strain would occur under the stress applied in a specific direction of the single crystal silicon thin film on the sapphire substrate.

The X-ray diffraction apparatus according to the present invention enables both the out-of-plane diffraction measurement and the in-plane diffraction measurement to be performed with the same apparatus, as shown in FIGS. 18A and 18B, with a high degree of resolution. As a result, the stress (i.e., strain) applied to the thin film crystal can be measured easily and precisely as against the prior art.

Figure 20A:
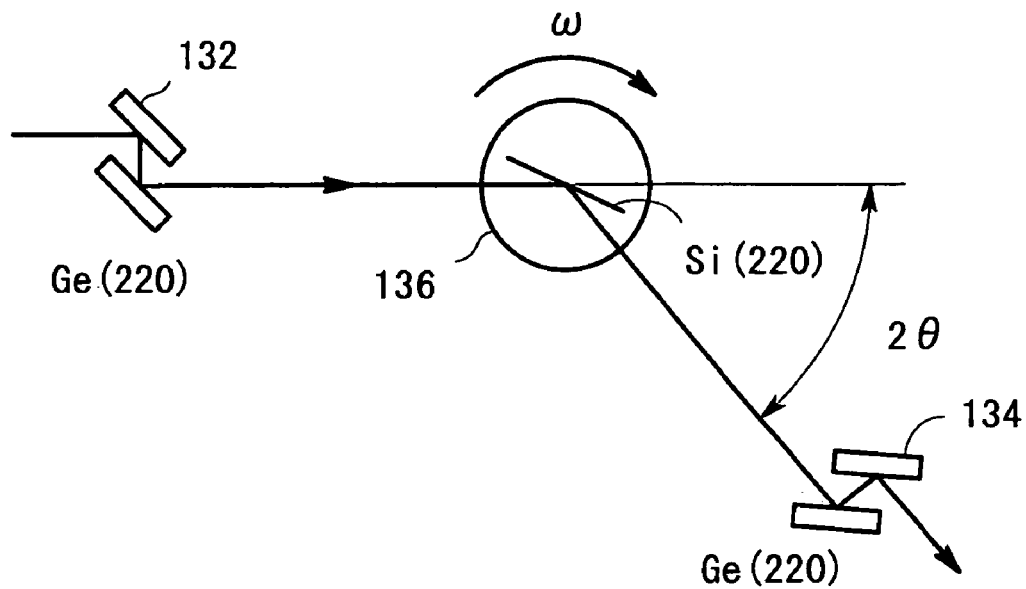
FIGS. 20A and 20B are layout drawings of a monochromator, an analyzer crystal and a sample in a measurement example 3 and a measurement example 4, respectively.

Next, measurement examples 3 and 4 will be described. In these examples, selected monochromators and samples were the same as those in the measurement example 2. In the measurement example 3, Si(220) diffraction of SOS was measured by the in-plane diffraction measurement. FIG. 20A shows an arrangement of the measurement example 3, in which 2θ was about 47.5°. In is noted that the sample 136 may be ω-rotated by 180° after the Si(220) diffraction measurement so as to measure Si(2,−2,0) diffraction too.

Figure 20B:
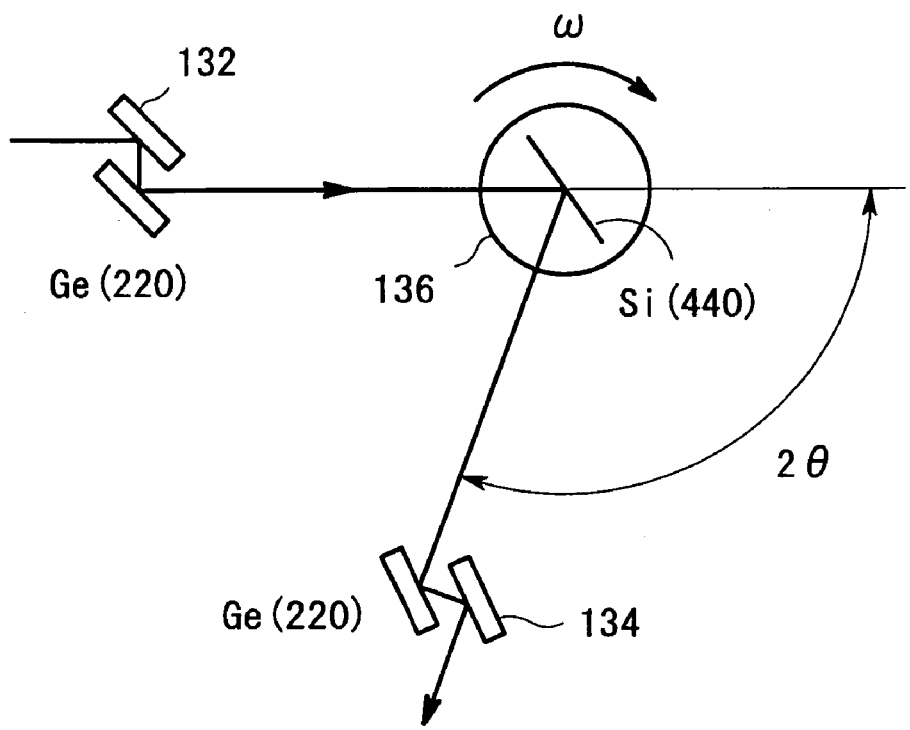

In the measurement example 4, Si(440) diffraction of SOS was measured by the in-plane diffraction measurement. FIG. 20B shows an arrangement of the measurement example 4, in which 2θ was about 107.4°. It is noted that the sample 136 may be ω-rotated by 180° after the Si(440) diffraction measurement so as to measure Si(4,−4,0) too.

Figure 21:
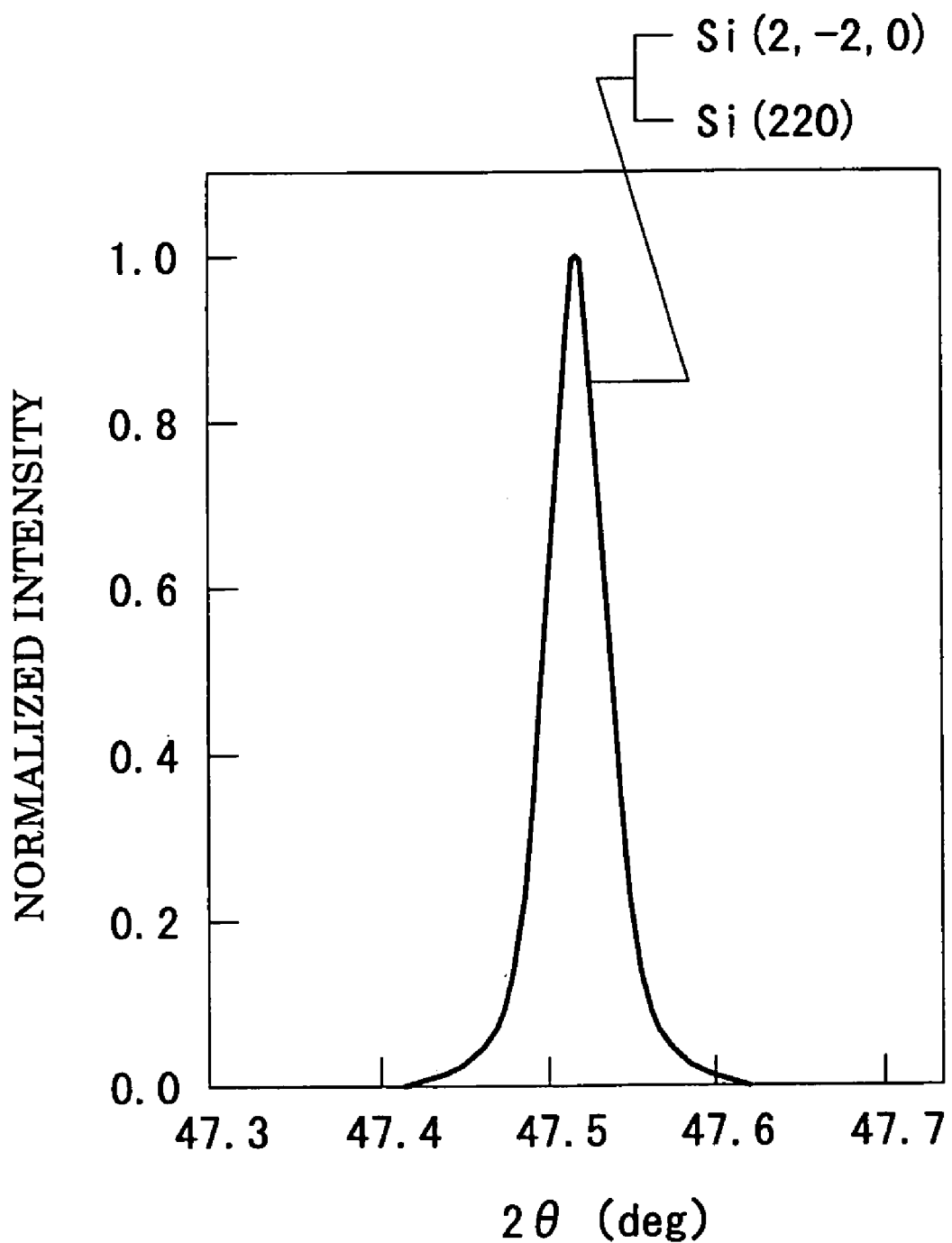
FIG. 21 is a graph of measured results in the measurement example 3.
Figure 22:
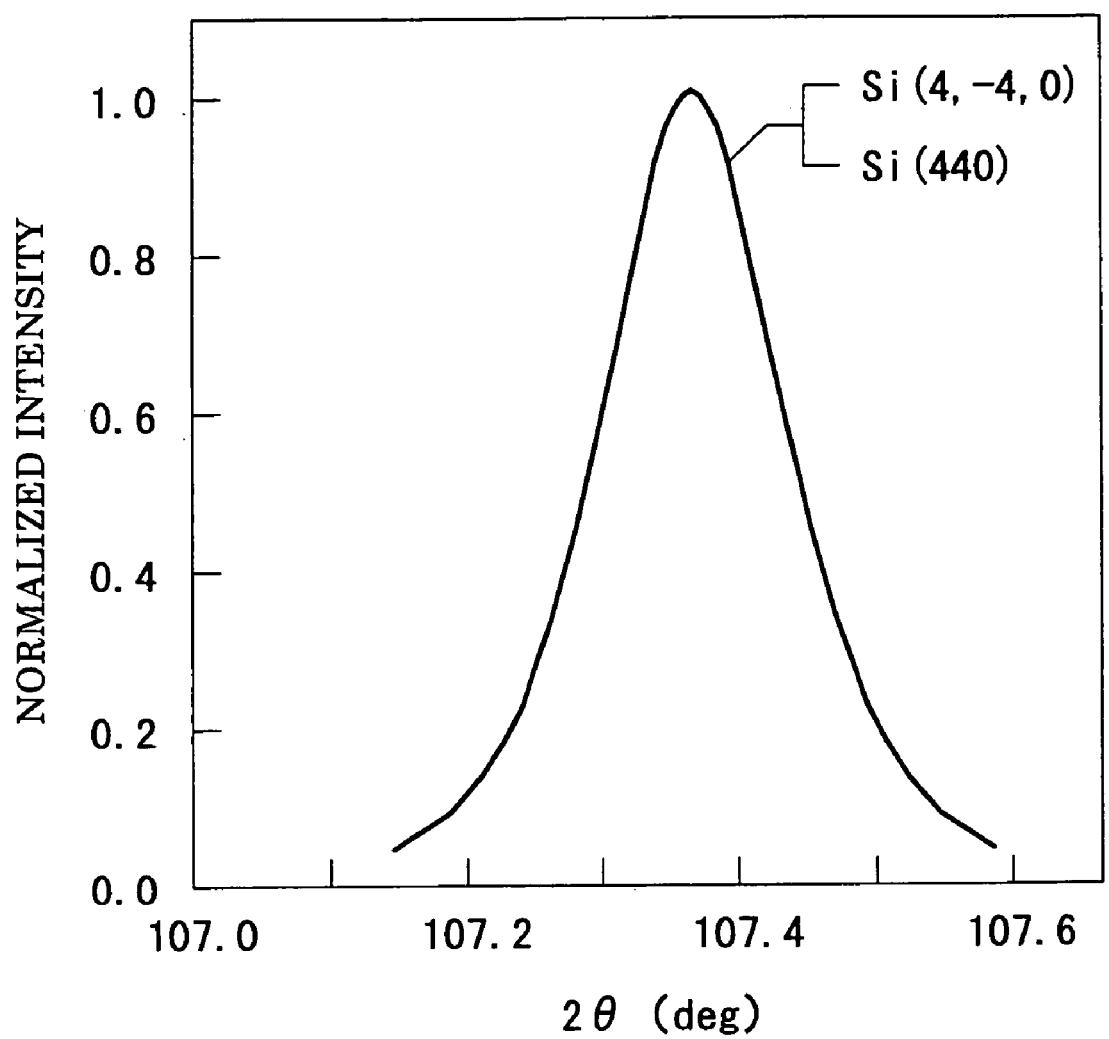
FIG. 22 is a graph of measured results in the measurement example 4.

FIG. 21 is a graph showing the measured result in the measurement example 3; and FIG. 22 is a graph showing the measured result in the measurement example 4.

Figure 23:
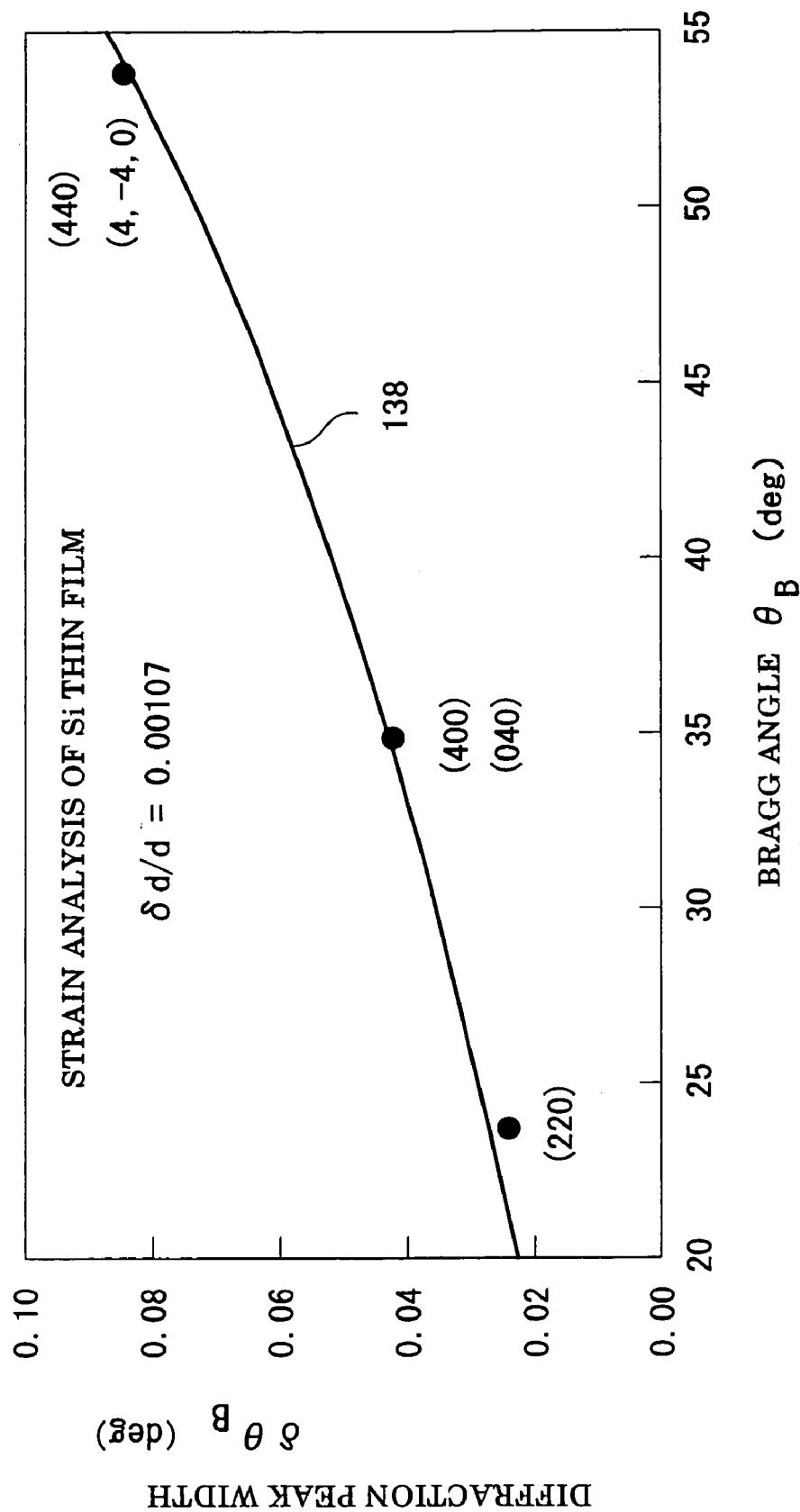
FIG. 23 is a graph of a strain analysis.

FIG. 23 is a graph for explaining the analysis of the stain in the samples based on the measurement examples 2 to 4. The abscissa indicates Bragg angles θB of respective lattice planes of the single crystal silicon thin film on the sapphire substrate, while the ordinate indicates diffraction peak widths δθB for respective Bragg angles. The diffraction peak width δθB is defined as FWHM of the diffraction peak. The graph shown in FIG. 19 for the measurement example 2 brings out the Bragg angle θB of the Si(400) and its diffraction peak width δθB, and this result is represented by a black circle at the center of the graph in FIG. 23. The graph shown in FIG. 21 for the measurement example 3 brings out the Bragg angle θB of the Si(220) and its diffraction peak width δθB, and this result is represented by another black circle on the left of the graph in FIG. 23. The graph shown in FIG. 22 for the measurement example 4 brings out the Bragg angle θB of the Si(440) and its diffraction peak width δθB, and this result is represented by further another black circle on the right of the graph in FIG. 23. A simulation curve 138 can be drawn on these measured values. it is understood from the simulation curve 138 that a nonuniform strain exists in the lattice constant in the in-plane direction and its value δd/d is 0.00107.

What is claimed is:

1. An X-ray diffraction apparatus in which:
   (a) said X-ray diffraction apparatus comprises an incident optical system, a sample support mechanism, a receiving optical system, and receiving-optical-system rotating means, and an X-ray emitted from the incident optical system is incident on a sample supported by the sample support mechanism, and an X-ray diffracted by the sample is detected by the receiving optical system;
   (b) the receiving-optical-system rotating means has a function to rotate the receiving optical system around a first axis of rotation for changing an angle which is defined by a direction of the X-ray incident on the sample and an optical axis of the receiving optical system;
   (c) the incident optical system includes an X-ray source and a multilayer-film mirror which has a function to collimate an X-ray emitted from the X-ray source within a plane perpendicular to the first axis of rotation;
   (d) the sample support mechanism includes attitude controlling means which has a function to switch a condition of the sample support mechanism from a state maintaining the sample to have a first attitude in which a normal line of the surface of the sample is substantially parallel with the first axis of rotation to another state maintaining the sample to have a second attitude in which the normal line of the surface of the sample is substantially perpendicular to the first axis of rotation;
   (e) the sample support mechanism includes first incident-angle controlling means which has a function to rotate the sample around a second axis of rotation which is substantially perpendicular to the first axis of rotation for changing an incident angle of an X-ray which is emitted from the incident optical system and is incident on the surface of the sample in the first attitude;
   (f) the sample support mechanism includes second incident-angle controlling means which has a function to rotate the sample around the first axis of rotation for changing the incident angle of an X-ray which is emitted from the incident optical system and is incident on the surface of the sample in the second attitude; and
   (g) the sample support mechanism includes an additional means for rotating the sample around two axes of rotation which are orthogonal to each other and pass on the surface of the sample.

2. An apparatus according to claim 1, wherein the attitude controlling means and the first incident-angle controlling means are actualized by a common mechanism.

3. An apparatus according to claim 1, wherein the multilayer-film mirror includes a first reflection surface with a parabolic shape for collimating an X-ray within a first plane perpendicular to the first axis of rotation and a second reflection surface with a parabolic shape for collimating an X-ray on a second plane perpendicular to the first plane.

4. An apparatus according to claim 1, wherein the multilayer-film mirror includes a first reflection surface with a parabolic shape for collimating an X-ray within a first plane perpendicular to the first axis of rotation and a second reflection surface with an elliptical-arc shape for focusing an X-ray on the sample within a second plane perpendicular to the first plane.

5. An apparatus according to claim 1, wherein the receiving optical system can turn around the second axis of rotation too.

6. An apparatus according to claim 1, wherein the sample support mechanism includes a mechanism for moving the sample in a direction perpendicular to the surface of the sample, a mechanism for translating the sample in a two-dimensional direction within a plane parallel with the surface of the sample, and a mechanism for an in-plane rotation of the sample.

7. An apparatus according to claim 1, wherein the attitude controlling means includes a curved guide having a circular-arc internal surface and an attitude-change table movable along the internal surface of the curved guide,
   the curved guide has one end which is located at a position higher than the sample and another end which is located at a position lower than the sample, and
   a through-hole through which the X-ray can pass is formed in a vicinity of the one end of the curved guide.

* * * * *